US007526415B2

(12) United States Patent
Shan et al.

(10) Patent No.: US 7,526,415 B2
(45) Date of Patent: Apr. 28, 2009

(54) GRID BASED COMPUTATION FOR MULTIPLE BODY SIMULATION.

(75) Inventors: Yibing Shan, Summit, NJ (US); John Klepeis, New Fairfield, CT (US); Michael Eastwood, New York, NY (US); Ron Dror, New York, NY (US); David E. Shaw, New York, NY (US)

(73) Assignee: D. E. Shaw Research, LLC, New York, NY (US)

( * ) Notice: Subject to any disclaimer, the term of this patent is extended or adjusted under 35 U.S.C. 154(b) by 408 days.

(21) Appl. No.: 11/171,634

(22) Filed: Jun. 30, 2005

(65) Prior Publication Data

US 2006/0142980 A1  Jun. 29, 2006

Related U.S. Application Data

(60) Provisional application No. 60/584,032, filed on Jun. 30, 2004, provisional application No. 60/584,000, filed on Jun. 30, 2004.

(51) Int. Cl.
  *G06F 7/60* (2006.01)
(52) U.S. Cl. .................... 703/2; 703/6; 703/11; 703/12
(58) Field of Classification Search .............. 703/2, 703/6, 11, 12
  See application file for complete search history.

(56) References Cited

U.S. PATENT DOCUMENTS 5,915,230 A * 6/1999 Berne et al. ............... 702/22
6,600,788 B1   7/2003 Dick et al.
7,096,167 B2 * 8/2006 Zhou et al. ................. 703/2

OTHER PUBLICATIONS

Abdulnour Y. Toukmaji et al., "Ewald summation techniques in perspective: a survey", 1996, Elsevier Science, Computer Physics Communications 95, pp. 73-92.*

Y.-J. Rhee et al., "Ewald methods in molecular dynamics for systems of finite extent in one of three dimensions", 1989, The American Physical Society, pp. 36-40.*

Markus Deserno et al., "How to mesh up Ewald sum (I): A theoretical and numerical comparison of various particle mesh routines", 1998, Max-Planck-Institut fur Polymerforschung, pp. 1-18.*

Snir, M., "A Note on N-Body Computations with Cutoffs," Theory of Computing Systems, Sprnger-Verlag USA, 37: 295-318 (2004).

Heffelfinger, G.S., "Parallel Atomistic Simulations," Computer Physics Communications, 128:219-237 (2000).

McCoy et al., "Parallel Particle Simulations of Thin-Film Deposition," International Journal of High Performance Computing Applications, 13:16-32 (1999).

Almasi et al., "Demonstrating the Scalability of a Molecular Dynamics Application on a Petaflops Computer," International Journal of Parallel Programming, 30:317-351 (2004).

(Continued)

*Primary Examiner*—Paul L Rodriguez
*Assistant Examiner*—Jason Proctor
(74) *Attorney, Agent, or Firm*—Occhiuti Rohlicek & Tsao LLP

(57) ABSTRACT

A method and a corresponding software and a system for processing a charge distribution according to a spreading function and a predefined operation are described.

115 Claims, 16 Drawing Sheets

OTHER PUBLICATIONS

Pande Visjay et al., "Atomistic Protein Folding Simulations on the Submillosecond Time Scale Using Worldwide Distributed Computing," Bioplymers 68:91-109 (2003).

Toukmaji et al., "Ewald Summation Techniques in Perspective: A Survey" Computer Physics Communications 95: 73-92 (1996).

Zaslavsky et al., "An Adaptive Multigrid Technique for Evaluating Long-Range Forces in Biomolecular Simulations," Applied Mathematics and Computation, 97:237-250 (1998).

Dehnen et al., "A Hierarchial 0(N) Force Calculation Algorithm," Journal of Computational Physics, 179: 27-42 (2002).

Darden et al., "New Tricks for Modelers from the Crystallography Toolkit: The Particle Mesh Ewald Algorithm and its use in Nucleic Acid Simulation," Structure with Folding and Design, vol. 7, No. 3, (ZP002358599) (1999).

Schlick et al., "Algorithmic Challenges in Computational Molecular Biophysics," Journal of Computational Physics, 151:9-48 (1999).

Sagui et al., "Molecular Dynamics Simulations of Biomolecules:Long-Range Electrostatic Effects," Annual Review of Biophysics and Biomolecular Structure, 28:155-179 (1999).

Greengard et al., "A New Version of the Fast Multipole Method for Screened Coulomb Interactions in Three Dimensions," Journal of Computational Physics, 180: 642-658 (2002).

Patent Cooperation Treaty, *PCT Notification of Transmittal of International Search Report*, PCT/US2006/032498, Mar. 30, 2007 (6 pages).

Patent Cooperation Treaty, *PCT Notification of Transmittal of International Search Report*, PCT/US2005/023184, Dec. 12, 2005 (2 pages).

Patent Cooperation Treaty, *Notification of Transmittal of International Preliminary Report on Patentability*, PCT/US2006/032498 Nov. 7, 2007 (14 pages).

Patent Cooperation Treaty, *PCT Notification of Transmittal of International Search Report*, PCT/US2006/014782, Jul. 26, 2006 (2 pages).

Beckers et al., "An Iterative PPPM Method for Simulating Coulombic Systems on Distributed Memory Parallel Computers," *Molecular Simulation*, 20:369-383 (1998).

Darden et al., "Particle Mesh Ewald: An N•log($N$) Method for Ewald Sums in Large Systems," *J. Chem. Phys.*, 98:10089-10092 (1993).

Deserno, Markus and Christian Holm, "How to Mesh Up Ewald Sums. II. An Accurate Error Estimate for the Particle-Particle-Particle-Mesh Algorithm," *Journal of Chemical Physics*, 109(18):7964-7701 (1998).

Essmann et al., "A Smooth Particle Mesh Ewald Method," *J. Chem. Phys.*, 103:8577-8593 (1995).

Greengard, L. and V. Rokhlin, "A Fast Algorithm for Particle Simulations," *Journal of Computational Physics*, 73:325-348 (1987).

Heyes, D.M., "Electrostatic Potentials and Fields in Infinite Point Charge Lattices," *J. Chem. Phys.* 74(3):1924-1929 (1981).

Maggs, A.C., and V. Rossetto, "Local Simulation Algorithms for Coulomb Interactions," *Phys. Rev. Lett.*, 88:196402 (2002).

Sagui, C., "Toward an Accurate Representation of Electrostatics in Classical Force Fields: Efficient Implementation of Multipolar Interactions in Biomolecular Simulations," *Journal of Chemical Physics*, 120(1): 73-87 (2004).

Sagui, Celeste and Thomas Darden, "Multigrid Methods for Classical Molecular Dynamics Simulations of Biomolecules," *Journal of Chemical Physics*, 114(15):6578-6591 (2001).

Skeel et al., "Multiple Grid Methods for Classical Molecular Dynamics," *J. Comput. Chem.*, 23:673-684 (2002).

Wolf et al., "Exact Method for the Simulation of Coulombic Systems by Spherically Truncated, Pairwise $r^{-1}$ Summation," *J. Chem. Phys.*, 110(17):8254-8282 (1999).

York, Darin, and Weitao Yang, "The Fast Fourier Poisson Method for Calculating Ewald Sums," *J. Chem. Phys.*, 101:3298-3300 (1994).

Cecchet, Emmanuel, "Memory Mapped Networks: A New Deal for Distributed Shared Memories? The SciFS Experience," *Proceedings of the IEEE International Conference on Cluster Computing*, Sep. 23-26, 2002, Piscataway, NJ USA, pp. 231-238 (XP010621880).

Culler et al., "Interconnection Network Design," *Parallel Computer Architecture- A Hardware/Software Approach*, Morgan Karufmann (1999) San Francisco, CA, pp. 749-778 (XP002333436).

Culler et al., *"Parallel Computer Architecture- A Hardware/Software Approach,"* Morgan Karufmann (1999) San Francisco, CA, pp. 25-52; 78-79; 166-174; 513-521; 822-825 (XP002417055).

Mukherjee et al., "Efficient Support for Irregular Applications on Distributed-Memory Machines," *ACM Sigplan Notices* 30:68-79 (1995).

Oral, S. and George, A., "A User-Level Multicast Performance Comparison of Scalable Coherent Interfaces and Myrinet Interconnects," *Proceedings of the 28th Annual IEEE International Conference on Local Computer Networks*, Oct. 20-24, 2003, Piscataway, NJ, USA, pp. 518-527 (XP010666014).

Reinhardt et al., "Hardware Support for Flexible Distributed Shared Memory," *IEEE Transactions on Computers* 47(10): 1056-1072 (1998).

\* cited by examiner

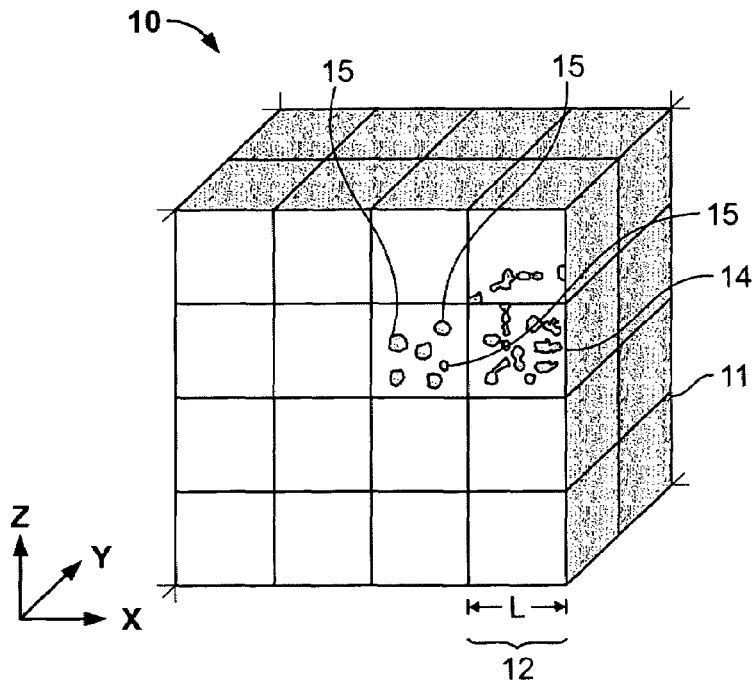

FIG. 1

$$N \text{ Charges } \{(q_i, r_i)\} \Rightarrow \varrho(r) = \sum_{i=1}^{N} q_i \, \delta(r-r_i) \quad (20)$$

+ Periodic copies $$= \sum_{i=1}^{N} \varrho_i(r)$$

(2) $\quad E = \frac{1}{2} \sum_{i=1}^{N} f_i(r_i) q_i \quad$ (Potential energy per unit box/ periodic copy) $\quad (22)$ (3) $\quad$ where $f_i(r_i) = \sum_{\substack{j=1 \\ j \neq i}}^{N} \sum_{n} \frac{q_j}{|r_i - (r_j + nL)|} \quad (24)$ Sum over periodic copies at (vector) displacement n unit boxes of size L.

$$F_i = -\frac{\partial E}{\partial r_i} \quad \text{(force on particle i)} \quad (26)$$

FIG. 2

$$(5) \quad f_i(r_i) = \int_{\text{All space}} \frac{\varrho(r) - \varrho_i(r)}{|r-r_i|} \, dr \qquad (28)$$

$$(7)\text{-}(10) \quad = \left[ \int \frac{-\varrho_{i\sigma}(r)}{|r-r_i|} \, dr \right] \qquad (30a)$$

$$+ \left[ \int \frac{(\varrho(r) - \varrho_i(r)) - (\varrho_\sigma(r) - (\varrho_{i\sigma}(r)))}{|r-r_i|} \, dr \right] \qquad (30b)$$

$$+ \left[ \int \frac{\varrho_\sigma(r)}{|r-r_i|} \, dr \right] \qquad (30c)$$

$$= \left[ -q_i \sqrt{2/\pi\sigma^2} \right] \quad \swarrow f_i^{\text{self}} \qquad (32a)$$

$$+ \left[ \sum_{\substack{j=1 \\ i \neq j}}^{N} q_j \frac{\text{erfc}(|r_i - r_j|/\sqrt{2}\sigma)}{|r_i - r_j|} + \text{Periodic copies} \right] \quad \swarrow f_i^{\text{dir}}(r_i) \qquad (32b)$$

$$+ \left[ \int \frac{\varrho_\sigma(r)}{|r-r_i|} \, dr \right] \quad \swarrow f_\sigma(r_i) \qquad (32c)$$

FIG. 3

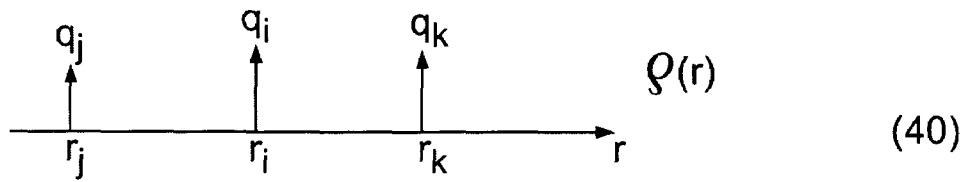
(40)
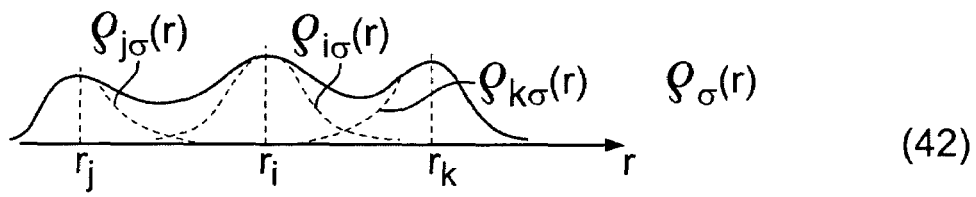
(42)
$$\rho_\sigma(r) = \rho(r) \otimes G_\sigma(r) \quad (44)$$
(46)
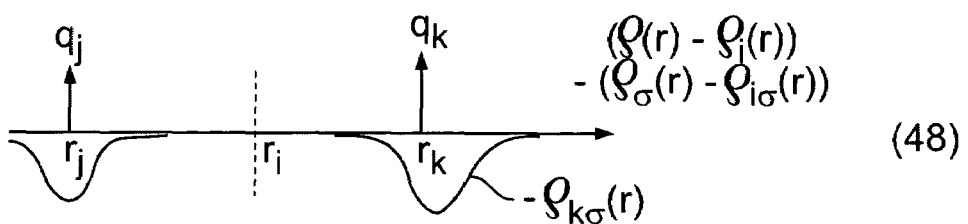
(48)
$$\rho(r) - \rho_i(r) = \overbrace{[-\rho_{i\sigma}(r)]}^{(46)} + \overbrace{[(\rho(r) - \rho_i(r)) - (\rho_\sigma(r) - \rho_{i\sigma}(r))]}^{(48)} + \overbrace{[\rho_\sigma(r)]}^{(42)}$$
(50)
FIG. 4

$$(11) \quad E = \frac{1}{2} \sum_{i=1}^{N} f_i(r_i) q_i \qquad (52)$$

$$= \left[ -\frac{\sum_i q_i^2}{\sqrt{2\pi\sigma^2}} \right] \qquad (54a)$$

$$+ \left[ \frac{1}{2} \sum_{i \neq j} \frac{q_i q_j \, \text{erfc}(|\Omega_i - \Omega_j|/\sqrt{2}\sigma)}{|r_i - r_2|} + \text{Periodic copy terms} \right] \qquad (54b) \Bigg\} E^{dir}$$

$$+ \left[ \frac{1}{2} \sum_{i=1}^{N} q_i f_\sigma(r_i) \right] \leftarrow E_\sigma \qquad (54c)$$

$$E_\sigma = \frac{1}{2} \int_{\text{Unit Volume}} \varrho(r) f_\sigma(r) dr = \frac{1}{2} \varrho(r) \cdot f_\sigma(r) \qquad (56)$$

$$F_i^\sigma = -\frac{\partial E_\sigma}{\partial r_i} = -\frac{\partial}{\partial r_i} \left( \frac{1}{2} \varrho(r) \cdot f_\sigma(r) \right) \qquad (58)$$

FIG. 5

$$f_\sigma(r) = \int \frac{\varrho_\sigma(r')}{|r-r'|} dr' \qquad (60)$$

$$\Downarrow$$

$$f_\sigma(r) = \varrho_\sigma(r) \otimes \gamma(r)$$
$$\text{where } \gamma(r) = \frac{1}{r} \qquad (62)$$

$$= \varrho(r) \otimes G_\sigma(r) \otimes \gamma(r) \qquad (64)$$

$$E_\sigma = \frac{1}{2} \varrho(r) \cdot (\varrho(r) \otimes G_\sigma(r) \otimes \gamma(r)) \qquad (66)$$

$$G_\sigma = G_{\sigma_A} \otimes G_{\sigma_B}$$

$$= \frac{1}{2} \underbrace{(\varrho(r) \otimes G_{\sigma_A})}_{\varrho_{\sigma_A}(r)} \cdot \underbrace{(\varrho(r) \otimes G_{\sigma_B} \otimes \gamma(r))}_{\varrho_{\sigma_B}(r)} \qquad (68)$$
$$\underbrace{\phantom{(\varrho(r) \otimes G_{\sigma_B} \otimes \gamma(r))}}_{f_{\sigma_B}}$$

$$F_i^\sigma = -\frac{\partial}{\partial r_i} \left( \frac{1}{2} \varrho_{\sigma_A}(r) \cdot f_{\sigma_B}(r) \right) \qquad (70)$$

FIG. 6

GRID BASED COMPUTATION FOR MULTIPLE BODY SIMULATION.

CROSS-REFERENCE TO RELATED APPLICATIONS

This application claims priority under 35 U.S.C. §119 to U.S. Provisional Patent Application Ser. No. 60/584,032, filed Jun. 30, 2004, and entitled "ORTHOGONAL METHOD" and to U.S. Provisional Patent Application Ser. No. 60/584,000, filed Jun. 30, 2004, and entitled "MULTIPLE BODY SIMULATION", the entire contents of which are hereby incorporated by reference.

This application is related to U.S. patent application Ser. No. 11/171,619 filed on Jun. 30, 2005 and to International Patent Application PCT/US05/23184 filed on Jun. 30, 2005.

TECHNICAL FIELD

This invention relates to simulation of multiple-body interactions.

BACKGROUND

Simulation of multiple-body interactions (often called "N-body" problems) are useful in a number of problem areas including celestial dynamics and computational chemistry. Biomolecular or electrostatic particle interaction simulations complement experiments by providing a uniquely detailed picture of the interactions between particles in a system. An important issue in simulations is the simulation speed.

Determining the interaction between all pairs of bodies in the system by enumerating the pairs can be computationally intensive, and thus, alternate interaction schemes are often used. For example, all particles within a predefined radius of a particular particle are interacted with that particle while particles farther away are ignored.

In some simulation schemes an Ewald method is used, which can reduce the amount of computation as opposed to enumeration of all potentially interacting pairs of bodies. For simulation of electrostatic systems, the Ewald method divides the electrostatic potential defined as a function of location into two main terms. A "screening" charge distribution, typically chosen to be Gaussian, is (notionally) centered on every point charge. This screening charge distribution is chosen to give the same charge magnitude but with opposite sign as the point charge on which it is centered. The electrostatic potential due to the combination of the point charge and the screening charge falls off rapidly with distance. Thus, this first contribution to the electrostatic potential can be neglected beyond a relatively small cut-off distance. The second contribution to the electrostatic potential is due to the negative of the contribution of all the screening charge distributions alone, essentially compensating for their introduction in the first term. This second contribution can be obtained by solving the Poisson equation for the charge distribution given by the sum of screening charge distributions.

SUMMARY

In one aspect, the invention includes a method and corresponding software and a system for processing a charge distribution according to a spreading function and a predefined operation. The spreading function is representable as a convolution of a first spreading function and a second spreading function, in which the first spreading function is different than the second spreading function. The processing of the charge distribution includes applying the first spreading function in a real domain to determine charge values at locations on the a grid from the charge distribution. The processing also includes applying the operation on the grid in the real domain and applying the second spreading function to the result of applying the operation.

Embodiments of the invention can include one or more of the following.

The spreading function can be mathematically represented by a variety of analytic functions. For example, the spreading function can be a Gaussian function, a polynomial function, an exponential function, a piecewise function, and the like.

The charge distribution can include a set of point charges. Each point charge of the set of point charges can have associated charge value ($q_i$) and an associated location ($r_i$). At least some of the associated locations ($r_i$) can be locations not on the grid.

Applying the first spreading function in the real domain to determine charge values at locations on the grid from the charge distribution can include convolving a distribution representing the set of point charges with the first spreading function. Convolving a distribution representing the set of point charges with a first spreading function can include computing a distribution according to $\rho(r) \otimes S(r)$, where $\rho(r)$ represents the charge distribution and $S(r)$ represents the first spreading function. Convolving a distribution representing the set of point charges with the first spreading function can include, for each point charge, spreading a charge associated with the point charge to a set of nearby grid locations.

Applying the operation on the grid in the real domain can include computing a potential function. Computing the potential function can include computing a potential value at at least some of the grid locations. The operation can include a convolution, for example, a convolution with a $1/r$ function. The operation can include a solution of a Poisson function. The operation can include a convolution with a third portion of the spreading function. A specific application of the operation can include computing a potential according to $\phi^*(r) = \rho^s(r) \otimes \gamma(r)$ where $\rho^s(r)$ depends on the charge distribution as well as the first spreading function and $\gamma(r)$ is an operator. The operator, $\gamma(r)$, can include a $1/r$ function.

Applying the second spreading function to the result of applying the operation can generate at least some force terms. At least some of the force terms can be associated with non-grid locations. The charge distribution can include a set of point charges at non-grid locations ($r_i$) and at least some of the force terms associated with non-grid locations can be associated with the non-grid locations ($r_i$) associated with the point charges. Applying the second spreading function to the result of applying the operation can include applying a spatial derivative to the result of applying the function.

Applying the second spreading function to the result of applying the operation can include evaluating a spatial derivative at grid locations. Evaluating the spatial derivative can include applying the spatial derivative to the result of applying the operation on the grid.

Applying the second spreading function to the result of applying the operation can include computing a potential energy. Applying the second spreading function to the result of applying the operation can include computing force values at locations off the grid based on values at the grid locations.

The real domain can be a real spatial domain.

Applying the first spreading function can include splitting the first spreading function into a first portion and a second portion, and applying the first spreading function can include applying the first portion to determine charge values at grid locations and applying the second portion to the values at the grid locations. The second portion can be implemented as a separable function. Splitting the first spreading function into the first portion and the second portion can be selected based on computational factors, such as computational complexity. The first portion can be equal to the second portion. In the alternative, the first portion can be unequal to the second portion. For example, the first portion can be smaller than the second portion. The first portion can be selected to include at least a minimum amount of the first spreading function needed to maintain an accuracy level for a force calculation or the first portion can be selected to be a larger portion of the first spreading function than needed to maintain an accuracy level for a force calculation.

The first spreading function, the second spreading, or both can be Gaussian functions. If both the first spreading function and the second spreading function are Gaussian functions, the Gaussian functions can have different variances.

The charge distribution can include a charge distribution for a molecule or system of molecules, such as a protein or a protein in a solution.

In another aspect, the invention can include a method and a corresponding software and a system for processing a charge distribution according to a spreading function and a predefined operation. The spreading function is representable as a convolution of a first spreading function and a second spreading function. The first spreading function can be represented in two portions, the second portion being a separable function. The method can also include applying the first portion of the first spreading function in a real domain to determine charge values at locations on the grid from the charge distribution, applying a second portion of the first spreading function in the real domain, and applying an operation in the real domain on the grid.

Embodiments of the invention can include one or more of the following.

The method can also include applying the second spreading function to the result of applying the operation.

The spreading function can be mathematically represented by a variety of analytic functions. For example, the spreading function can be a Gaussian function, a polynomial function, an exponential function, a piecewise function, and the like.

The charge distribution can include a set of point charges. Each point charge in the set of point charges can have an associated charge value (qi) and an associated location (ri). At least some of the associated locations (ri) can be locations not on the grid.

Applying the first portion of the first spreading function in the real domain to determine charge values at locations on the grid from the charge distribution can include convolving a distribution representing the set of point charges with the first portion of the first spreading function. Convolving the distribution representing the set of point charges with the first portion of the first spreading function can include computing a distribution according to $\rho(r) \otimes S(r)$ where $\rho(r)$ includes the charge distribution and $S(r)$ includes the first portion of the first spreading function. Convolving a distribution representing the set of point charges with the first portion of the first spreading function can include, for each point charge, spreading a charge associated with the point charge to a set of nearby nodes or the gird. Applying the second portion of the first spreading function in the real domain can include applying the second portion of the first spreading function as a separable function. Applying the second potion of the first spreading function in the real domain can include implementing a discrete space convolution. Applying the second portion of the first spreading function can spread charges over the grid locations.

Applying the operation on the grid in the real domain can include computing a potential function. Computing a potential function can include computing a potential function at the grid locations. The operation can include a convolution, for example, a convolution with a $1/r$ function. In another example, the operation can include a solution of a Poisson function. In another example, the operation can include a convolution with the second portion of the first spreading function. A specific application of the operation can include computing a potential according to $\phi^*(r) = \rho^s(r) \otimes \gamma(r)$ where $\rho^s(r)$ depends on the charge distribution as well as the first spreading function and $\gamma(r)$ is an operator. The operator, $\gamma(r)$, can include a $1/r$ function.

Applying the second spreading function to the result of applying the operation can generate at least some force terms. At least some of the force terms can be associated with non-grid locations. Alternately, or in addition other force terms can be associated with grid locations. The charge distribution can include a set of point charges at non-grid locations (ri) and the force terms at non-grid locations can be at the non-grid locations (ri) associated with the point charges. Applying the second spreading function to the result of applying the operation can include calculating a spatial derivative at grid locations. Evaluating the spatial derivative can include applying the spatial derivative to the result of applying the operation on the grid. The real domain can be a real spatial domain. Applying the second spreading function can include computing force values at locations off the grid based on values at the grid locations.

The first spreading function can be represented as a different distribution than the second spreading function. The first spreading function and/or the second spreading function can be Gaussian functions. For example, the first spreading function and the second spreading function can both be Gaussian functions each having a different variance. The first portion can be equal to the second portion. Alternately, the first portion can be unequal to the second portion. For example, the first portion can be smaller than the second portion. The first portion can include at least a minimum amount of the first spreading function needed to maintain an accuracy level.

Applying an operation in the real domain on the grid can include solving Poisson's equation. Solving Poisson's equation can include iteratively solving Poisson's equation. The charge distribution can include a charge distribution for a molecule or system of molecules, such as a protein or a protein in a solution.

In another aspect, the invention can include a method for molecular simulation or modeling, such as protein simulation, that includes computing force or charge on particles in a molecule. Computing the forces can include processing a charge distribution as described herein.

In another aspect, the invention can include a method for molecular simulation or modeling, such as protein simulation, that includes the application of an Ewald method and includes processing a charge distribution as described herein.

In another aspect, the invention can include a method for molecular simulation or modeling, such as protein simulation, that includes the application of a direct enumeration of pairs as described herein and also includes processing a charge distribution according to one or more of the methods described herein.

In another aspect, the invention can include a method and a corresponding software and a system for processing a charge distribution according to a Gaussian spreading function. The Gaussian spreading function can be a convolution of components. The processing can include spreading charges to the grid in a first domain based on a first component of the Gaussian spreading function. The processing can also include applying a function to the charges on the grid in a second domain using a second component of the Gaussian spreading function and performing a calculation based on a third component of the Gaussian spreading function and the result of applying the function.

Embodiments of the invention can include one or more of the following.

The spreading function can alternately be mathematically represented by a variety of analytic functions. For example, the spreading function can be a non-Gaussian function such as a polynomial function, an exponential function, a piecewise function, and the like.

The charge distribution can include a set of point charges. Each point charge included in the set of point charges can have an associated charge value (qi) and an associated location (ri). At least some of the associated locations (ri) can be locations not on the grid.

Spreading the charges to the grid can include convolving a distribution representing the set of point charges with the first component of the spreading function. Convolving a distribution representing the set of point charges with the first component of the spreading function can include computing a distribution according to $\rho(r) \otimes S(r)$ where $\rho(r)$ represents the charge distribution and $S(r)$ represents the first component of the spreading function. Convolving a distribution representing the set of point charges with the first component of the spreading function can include, for each point charge, spreading the charge to a set of nearby grid locations.

Applying the function to the charges on the grid in a second domain can include applying the second component of the spreading function as a separable function. Applying the second component can include implementing a discrete space convolution. Applying the function to the charges on the grid can spread charges over the grid locations. Applying the function to the charges on the grid in the second domain can include computing a potential function. Computing the potential function can include computing the potential function at the grid locations. A specific application of the operation can include computing a potential according to $\phi^*(r)=\rho^s(r) \otimes \gamma(r)$ where $\rho^s(r)$ depends on the charge distribution as well as the first spreading function and $\gamma(r)$ is an operator. The operator, $\gamma(r)$, can include a 1/r function.

The operation can include a convolution, for example, a convolution with a 1/r function. In another example, the operation can include a solution of a Poisson function. In another example, the operation can include a convolution with a second portion of the first spreading function.

Performing the calculation based on a third component of the Gaussian spreading function and the result of applying the function can generate at least some force terms. At least some of the force terms can be associated with non-grid locations. In some embodiments, the charge distribution can include a set of point charges at non-grid locations (ri) and the force terms at non-grid locations are at the non-grid locations (ri) associated with the point charges.

Applying the second spreading function to the result of applying the operation can include evaluating a spatial derivative at grid locations. Evaluating the spatial derivative can include applying the spatial derivative to the result of applying the operation on the grid.

Performing the calculation based on a third component and the result of applying the function can include implementing a convolution of the result with the third component.

The first component of the Gaussian spreading function, the second portion of the Gaussian spreading function and the third portion of the Gaussian spreading function can each represent different Gaussian distributions. The first domain can be a real domain. The second domain can be an FFT domain.

Applying the function to the charges on the grid in the second domain using the second component of the Gaussian spreading function can include convolving the function with the second portion of the Gaussian spreading function. Convolving the function with the second portion of the Gaussian spreading function can include multiplying the function with the second portion of the Gaussian spreading function in the FFT domain. Performing the calculation can include calculating a force.

The charge distribution can include a charge distribution for a molecule or system of molecules, such as a protein or a protein in a solution.

In another aspect, the invention includes a method and a corresponding software and a system for selecting a first distribution, a second distribution, and a third distribution such that a convolution of the first distribution, the second distribution, and the third distribution is equal to a predefined spreading function. The method can also include determining forces on a particle associated with charges based on applying the first distribution and the second distribution in a first computational domain and applying the third distribution in a second computational domain. The spreading function can be mathematically represented by a variety of analytic functions.

Embodiments of the invention can include one or more of the following.

The spreading function can be a Gaussian function, a polynomial function, an exponential function, a piecewise function, and the like. Determining forces on the particle associated with the charges can include computing charge values at grid locations. Determining forces on the particle associated with the charges can include computing potentials at non-grid locations. In another embodiment, determining forces on the particle associated with the charges can include computing force terms at grid locations.

Applying the third distribution can include applying the third distribution in combination with an operation to the spread charge. The first distribution, the second distribution, and the third distribution can be Gaussian functions. Alternately, the first distribution, the second distribution, and the third distribution can be non-Gaussian functions such as polynomials, exponentials, or other functions. Selecting the distributions can include selecting the first distribution, the second distribution, and the third distribution based on an acceptable amount of error.

The operation can include, for example, a convolution with a 1/r function or a solution of a Poisson function. Applying the first distribution and the second distribution in a first computational domain can include convolving at least one of the first distribution and the second distribution with the charge distribution. Applying the third distribution in a second computational domain can include convolving the third distribution with a set of charges located at grid locations. The first domain can be a real domain and/or the second domain can be an FFT domain.

The Gaussian split Ewald (GSE) method provides a method for determining the interaction between two particles in a system that is fast when combined with a real space solution of Poisson's equation.

In a system, screening charge distributions that span many mesh points and methods to solve for the interaction and forces on a particle require a large number of grid operations per atom or particle in the system. In order to reduce the amount of calculation needed to determine the forces on a particle, the GSE method provides a two-stage approach. In the two-stage approach, a particle's charge is first spread to a small number of mesh points that lie within a restricted neighborhood of the particle. The additional broadening or spreading can be obtained in a second stage by a convolution operation. The convolution provides an advantage in the calculation time because when performed in reciprocal space the convolution does not add significant calculation time. In the GSE method, the Guassian function is divided between multiple portions of the overall calculation. Tuning the ratio between the portions of the Gaussian provides the advantage of allowing the computational load to be shifted away from the charge-spreading and interpolation steps to the highly efficient second charge spreading step. This takes advantage of the fact that an on-grid convolution with a Gaussian is less computationally intensive than other comparable methods.

In some examples, the Ewald mesh method may be combined with a real-space Poisson solver. The charge spreading and force calculation steps may be performed with a computational burden similar to that of efficient FFT-based approaches. Additional advantages are related to the reuse of the charge-spreading and force calculation algorithms in combination with a reciprocal space solution of the Poisson equation to give an Ewald method (k-GSE) that is conceptually simpler (and easier to implement) than the other methods without sacrificing performance.

The systems and methods described herein may have advantages for the simulation and modeling of a protein or proteins in a solution (e.g., a solvent). A protein in a solution can, for example, be amenable to periodic boundary conditions. In addition, such a system can provide a relatively uniform distribution of bodies to nodes within the system. For example, each node can include at least some bodies.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a block diagram.

FIGS. 2 and 3 are diagrams with a derivation of forces.

FIG. 4 is a diagram illustrating an Ewald decomposition.

FIGS. 5 and 6 are diagrams with equations related to an Ewald decomposition.

DETAILED DESCRIPTION

Figure 7A:
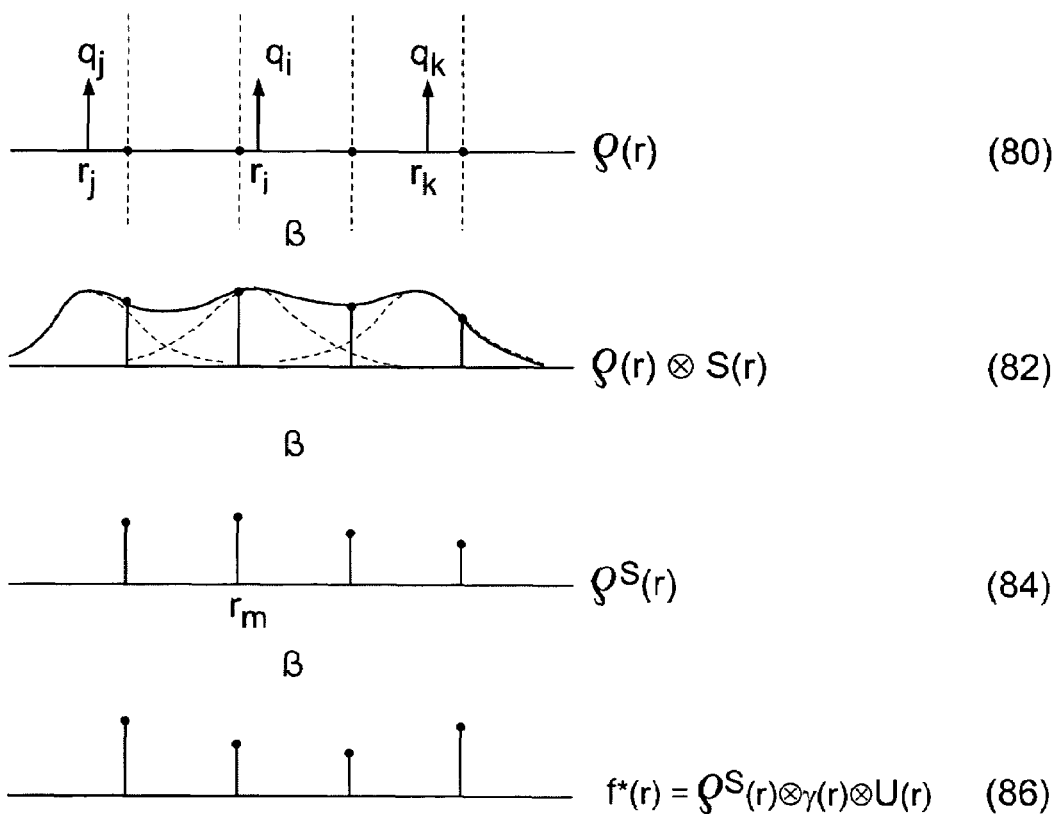
FIGS. 7A-7C are diagrams illustrating a mesh Ewald approach.

Referring to FIG. 1, N point charges 14 $\{q_i\}$ at positions $\{r_i\}$ are located in a cubic volume 11 of side length (L) 12. The system is assumed to be neutral, i.e.

$$\sum_{i=1}^{N} q_i = 0.$$

In order to avoid modeling discontinuities at the boundaries of the cubic volume, periodic boundary conditions are imposed such that copies of the original system (which we term boxes, the original being the "primary box" 11) tile an infinite space 10 in a cubic lattice so that particle i and its images 15 lie at $r_i + nL$, where $n = (n_x, n_y, n_z)$, with $n_\alpha = 0, \pm 1, \pm 2, \ldots, \pm \infty$ ($\alpha = x, y, $ or $z$). The assumption of cubic boxes is made to simplify the exposition; however, the method can be extended to other box geometries.

Referring to FIG. 2, one approach to computing the (vector) force on each particle is to first compute the total electrostatic potential energy E, per box, (eq. 22). The force on the $i^{th}$ particle in the box, $F_i$, is then computed using the partial derivative of the potential energy with respect to perturbation of the location, $r_i$, of that particle (eq. 26).

The total electrostatic energy per box in units where $4\pi\epsilon_0 = 1$ is $$E = \frac{1}{2} \sum_{i,j=1}^{N} {\sum_n}' \frac{q_i q_j}{|r_i - r_j - nL|}. \quad (1)$$

where the prime in the summation indicates that terms which simultaneously satisfy $n=0$ and $i=j$ are omitted from the sum. The most straightforward method of evaluating equation (1) and the corresponding forces is a straight cut-off method, i.e. to simply ignore terms in the sum with $|r_i - r_j - nL|$ greater than a cut-off distance. Unfortunately, the slow decay of the Coulomb potential can lead to artifacts in dynamical simulations, at least for cut-off radii small enough to allow rapid computation of the sum.

Ewald Sum

An alternative method for evaluating Equation (1) is the method of Ewald as described below.

The summation of Equation (1) is only conditionally convergent so strictly speaking we should start by defining exactly what we mean by it, for example by including a convergence factor. A concise and transparent description is given to follow. The summation of Equation (1) may be equivalently written as $$E = \frac{1}{2} \sum_{i=1}^{N} \phi_i(r) q_i \quad (2)$$

where by definition $$\phi_i(r_i) = \sum_{j=1}^{N} {\sum_n}' \frac{q_j}{|r_i - r_j - nL|} \quad (3)$$

is the electrostatic potential due to all charges at $r_i$ (omitting the charge at $r_i$ itself, as indicated by the prime on the sum). The charge distribution (over the complete volume) is simply a sum of delta functions, $$\rho(r) = \sum_{i=1}^{N} \sum_{n} q_i \delta(r - r_i - nL), \quad (4)$$

and $\phi_i(r_i)$ may be written in terms of the charge distribution as $$\phi_i(r_i) = \int_{-\infty}^{\infty} \frac{\rho(r) - \rho_i(r)}{|r_i - r|} d^3 r, \quad (5)$$

where $\rho_i(r) = q_i \delta((r - r_i))$ is introduced to avoid including self-interaction of the $i^{th}$ particle.

Referring to FIGS. 3 and 4, the Ewald decomposition may be considered to arise from adding and subtracting a screening charge distribution to the numerator of Equation (5), reproduced in FIG. 3 as equation (28). The screening charge distribution is defined as to be $-\rho_\sigma(r)$ where we define $$\rho_\sigma(r) = \sum_{i=1}^{N} \sum_{n} q_i \left(\frac{1}{2\pi\sigma^2}\right)^{3/2} \exp(-|r - r_i - nL|^2 / 2\sigma^2) \quad (6)$$

to be the "spread charge distribution" since it is simply the original charge distribution with the point charges spread into Gaussian charge distributions. We also define $$\rho_{i\sigma}(r) = q_i \left(\frac{1}{2\pi\sigma^2}\right)^{3/2} \exp(-|r - r_i|^2 / 2\sigma^2),$$

analogously to the definition of $\rho_i(r)$ above. Shapes other than Gaussians can alternately be used, however, the description will focus on the Gaussian form.

Referring to FIG. 4, the initial point charge distribution $\rho(r)$ (C1) includes impulses at the charge locations $\{r_i\}$, illustrated in FIG. 4 in one dimension for simplicity of presentation but representing the three-dimensional characteristics. The spread distribution $\rho_\sigma(r)$ (42) is the sum of the components $\rho_{i\sigma}(r)$ and their periodic copies, each of which has a Gaussian form.

The distribution $\rho(r) - \rho_i(r)$, which is essentially the impulses shown in (40) omitting the impulse at $r_i$, is decomposed into a sum of three terms:

- $-\rho_{i\sigma}(r)$, illustrated as (46);
- $\{\rho(r) - \rho_i(r)\} - \{\rho_\sigma(r) - \rho_{i\sigma}(r)\}$, illustrated as (48); and
- $\rho_\sigma(r)$ itself, illustrated as (42).

Referring back to FIG. 3, the integral $$\phi_i(r_i) = \int_{-\infty}^{\infty} \frac{\rho(r) - \rho_i(r)}{|r_i - r|} d^3 r$$

(28) is decomposed into a sum of three integrals (30a, 30b and 30c) corresponding to the three terms, which result in three terms (32a, 32b, and 32c). The electrostatic potential can therefore be rewritten as $$\phi_i(r_i) = \phi_i^{self} + \phi_i^{dir}(r_i) + \phi_\sigma(r_i), \quad (7)$$

where the first term arises to cancel self-interactions present in the third term and it is given by $$\phi_i^{self} = \int_{-\infty}^{\infty} \frac{-\rho_{i\sigma}(r)}{|r_i - r|} d^3 r = -q_i \sqrt{\frac{2}{\pi\sigma^2}}. \quad (8)$$

The second term is the direct contribution, which arises from the screened charge distribution, $$\phi_i^{dir}(r_i) = \int_{-\infty}^{\infty} \frac{\{\rho(r) - \rho_i(r)\} - \{\rho_\sigma(r) - \rho_{i\sigma}(r)\}}{|r_i - r|} d^3 r \quad (9)$$

$$= \sum_{j=1}^{N} q_j \sum_{n}' \frac{erfc(|r_i - r_j - nL| / \sqrt{2}\sigma)}{|r_i - r_j - nL|}$$

where erfc denotes the complementary error function, and the second equality in equation (9) follows after some algebra. Since $$erfc(x) = \frac{2}{\sqrt{\pi}} \int_{x}^{\infty} e^{-t^2} dt$$

decays rapidly with x, terms with $|r_i - r_j - nL|$ larger than some cut-off value [to be determined by $\sigma$ and the accuracy requirement] may be safely omitted from the sum, which may thus be evaluated as a direct sum in real space. The third term is the long range contribution, $$\phi_\sigma(r_i) = \int_{-\infty}^{\infty} \frac{\rho_\sigma(r)}{|r_i - r|} d^3 r. \quad (10)$$

Referring to FIG. 5, using equations (2) and (7), the total energy may likewise be split into three terms (54a, 54b, and 54c), $$E = \frac{-\sum_{i=1}^{N} q_i^2}{\sqrt{2\pi\sigma^2}} + \frac{1}{2} \sum_{i,j=1}^{N} \sum_{n}' \frac{q_i q_j erfc(|r_i - r_j - nL| / \sqrt{2}\sigma)}{|r_i - r_j - nL|} + \frac{1}{2} \sum_{i=1}^{N} \phi_\sigma(r_i) q_i \quad (11)$$

corresponding to self-interaction correction, direct sum and long-range contributions, respectively. The direct sum term is computed through direct enumeration of the interacting pairs. Various techniques can be used to evaluate this enumerated sum, including an "orthogonal method" that is described later in this document.

Although all three contributions to the electrostatic potential depend on $\sigma$, we have chosen to denote the long-range potential $\phi_\sigma(r)$ to emphasize its connection to the smoothly varying spread charge distribution $\rho_\sigma(r)$ through the Poisson equation $\nabla^2 \phi_\sigma = -4\pi\rho_\sigma$, the formal solution of which is Equation (10). Since $\rho_\sigma(r)$ is smoothly varying for all r, it can be represented in reciprocal (transform) space with a finite number of wave-number terms, or on a grid in real-space. The actual value of the grid spacing (or number of k-space terms) depends on both the overall accuracy required, and the value of σ. For fixed accuracy requirements, larger values of σ require larger cut-offs in the direct sum, but allow $\rho_\sigma(r)$ to be represented on a coarser grid (or with fewer k-space terms). Tuning σ therefore allows weight to be shifted between the direct and reciprocal summations, and σ is normally chosen to minimize the cost of the total computation. The calculation of the long-range contribution to the potential and the corresponding contributions to the energy and forces are discussed below.

Reformulation of Reciprocal Sum with Convolutions

The third term of the Ewald energy term is referred to as the "reciprocal sum" term:

$$E_\sigma = \frac{1}{2}\sum_{i=1}^{N} q_i \phi_\sigma(r_i) \text{ where } \phi_\sigma(r_i) = \int \frac{\rho_\sigma(r)}{|r - r_i|} dr$$

This term can be formulated in terms of convolutions allowing the establishment of relations (and a notation) useful in the discussion below related to mesh operations. A convolution of two real space quantities is denoted by the symbol $\otimes$, $$A \otimes B = \int_{-\infty}^{\infty} A(r - r')B(r')d^3 r'. \tag{12}$$

In the reciprocal (transform) space, convolution becomes multiplication, therefore, if $A \otimes B = C$ then $\tilde{A}\tilde{B} = \tilde{C}$, where we use the tilde to denote reciprocal space quantities, $$\tilde{A}(k) = \int_{-\infty}^{\infty} A(r) e^{-ik \cdot r} d^3 r.$$

Defining $\gamma(r) = 1/r$ and denoting the normalized Gaussian $G_\sigma(r) = (2\pi\sigma^2)^{-3/2} \exp(-r^2/2\sigma^2)$, we will need $$\tilde{\gamma} = 4\pi/k^2 \text{ and } \tilde{G}_\sigma = \exp(-\sigma^2 k^2/2), \tag{13}$$

where $k = |k|$ and $r = |r|$. The Fourier coefficients of periodic quantities (i.e. quantities that are identical in every box such as the charge density) are denoted with a subscript wavevector rather than an argument, so by definition $$\tilde{A}_k = \frac{1}{V}\int_V A(r) e^{-ik \cdot r} d^3 r,$$

where $$\int_V d^3 r$$

denotes an integral over the primary box of volume $V = L^3$. In particular, the Fourier representation of the original point charge density (the structure factor) is $$\tilde{\rho}_k = \frac{1}{V}\sum_{i=1}^{N} q_i e^{-ik \cdot r_i}. \tag{14}$$

It is also convenient to define the operation · between two periodic quantities as $$A \cdot B = \int_A A(r)B(r)d^3 r = V\sum_k \tilde{A}_k \tilde{B}_{-k} \tag{15}$$

where $k = 2\pi n/L$, and each of the three components of n runs over all integers. It follows from these definitions that if B is an even function (like γ or $G_\sigma$) and A and C are periodic (like ρ or $\rho_\sigma$) then $$A \cdot (B \otimes C) = (A \otimes B) \cdot C. \tag{16}$$

It is convenient to write the reciprocal Ewald sum using the notation defined above.

Referring to FIG. 6 (equations 60, 62, 64), $\rho_\sigma$ is ρ convolved with a normalized Gaussian of standard deviation σ:

$$\rho_\sigma = \rho \otimes G_\sigma.$$

The long-range contribution to the electrostatic potential is (from equation (5)) the charge density $\rho_\sigma$ convolved with the Green function $\gamma = 1/r$, $$\phi_\sigma = \rho_\sigma \otimes \gamma = \rho \otimes G_\sigma \otimes \gamma, \tag{17}$$

which is simply the formal solution to the Poisson equation for the spread charge distribution.

Referring to equations 66 in FIG. 6, the reciprocal sum contribution to the energy is given by $$E_\sigma = \frac{1}{2}\rho \cdot \phi_\sigma = \frac{1}{2}\rho \cdot (\rho \otimes G_\sigma \otimes \gamma). \tag{18}$$

Referring to equations 66, 67 and 68 in FIG. 6, if two quantities $\sigma_A$ and $\sigma_B$ are chosen such that $\sigma_A^2 + \sigma_B^2 = \sigma^2$ (and therefore $G_{\sigma_A} \otimes G_{\sigma_B} = G_\sigma$), using Equation (16) the energy can be rewritten by substitution and reordering terms as $$E_\sigma = \frac{1}{2}(\rho \otimes G_{\sigma_A}) \cdot (\rho \otimes G_{\sigma_B} \otimes \gamma) \tag{19}$$
$$= \frac{1}{2}\rho_{\sigma_A} \cdot (\rho_{\sigma_B} \otimes \gamma) = \frac{1}{2}\rho_{\sigma_A} \cdot \phi_{\sigma_B}.$$

In physical terms this means that the reciprocal sum energy, which can be thought of as the energy of the point charges interacting with the potential field due to (minus) the screening charge distribution, is equivalent to the interaction of Gaussian distributed charges with the electrostatic potential due to a screening charge distribution built from more narrowly distributed charges. While the constraint $\sigma_A^2 + \sigma_B^2 = \sigma^2$ means that $\sigma_A$ and $\sigma_B$ cannot both be chosen independently, and the energy is independent of the ratio $\sigma_A/\sigma_B$ which may chosen freely. Note that the reciprocal sum contribution to the force on particle i may be also written in terms of $\phi_{\sigma_B}$ as $$F_i^\sigma = -\frac{\partial E_\sigma}{\partial r_i} = -\frac{\partial \rho_{\sigma_A}}{\partial r_i} \cdot \varphi_{\sigma_B} \quad (20)$$

where again we have used Equation (16).

The convenience of the compact notation will become apparent when we additionally consider mesh operations, since these additional operations may also be written as convolutions. The ability to rewrite the energy in different forms, in a similar way to described above, allows computational weight to be shifted between different convolutions and gives a tunable parameter (similar to $\sigma_A/\sigma_B$) which may be varied to minimize the total computational burden. Without using a mesh-based method, the basic Ewald method is $O(N^2)$ for fixed $\sigma$. For example, substituting from the basic definitions into Equation (18) or Equation (19) gives $$E_\sigma = \frac{2\pi}{V} \sum_k' \frac{e^{-\sigma^2 k^2/2}}{k^2} |\tilde{\rho}_k|^2. \quad (21)$$

(As is common practice, we omit the k=0 term as indicated by the prime on the sum, and do so consistently throughout this paper. A more rigorous analysis shows how the k=0 term depends on the boundary conditions at infinity, its omission corresponding to "tin-foil boundary conditions".) For a given $\sigma$ and accuracy requirement the number of values of k which must be summed over is proportional N. Obtaining the Fourier representation of the charge density, i.e $\tilde{\rho}_k$, over this range using Equation (14) directly is thus $O(N^2)$. As mentioned in the introduction, increasing a can transfer computational burden to the O(N) direct sum, leading to an overall $O(N^{3/2})$ method, but for the number of particles in typical bimolecular simulations a significant increase in computation speed can be made by using mesh methods.

Ewald Mesh Methods

There are two classes of mesh-based methods. Real space (spatial domain) mesh methods take advantage of fast finite-difference Poisson solvers to solve the Poisson equation in real space. The other class, FFT based methods, solve the Poisson equation in reciprocal space using FFTs to transform a charge density to reciprocal space and inverse FFTs to transform the electrostatic potential back to real space. Both approaches are explained in more detail below, but first we briefly describe two operations common to both: going from an off-mesh to on-mesh charge distribution (charge spreading), and conversely going from a potential defined on-mesh to the forces on the off-mesh particles. Each of these operations may be written as a convolution. An optimal choice of convolution kernel for what are sometimes called the discretization and interpolation steps is known to be crucial for the efficiency and accuracy of an Ewald mesh method.

Figure 7B:
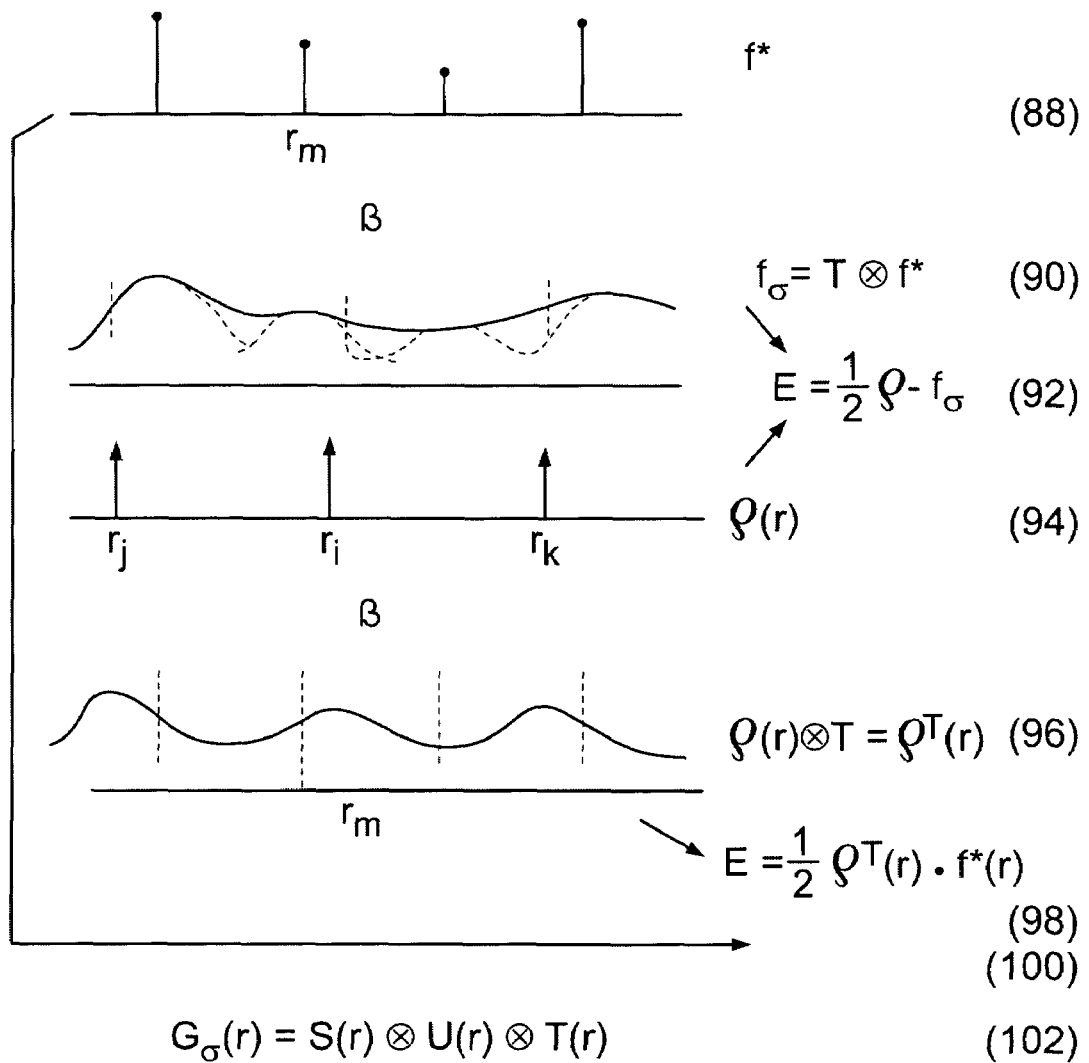

Referring to FIGS. 7A-7B, a representative discrete charge distribution $\rho(r)$ is illustrated with three point charges (80). For charge-spreading, an on-mesh charge distribution $\rho^S(r)$, which is defined at the discrete grid locations, is created by convolving the point charge distribution with a charge spreading function S (82) and sampling the result of the convolution (84):

$$\rho^S(r_m) = S \otimes \rho \quad (22)$$
$$= \int_{-\infty}^{\infty} S(r_m - r)\rho(r)d^3r$$
$$= \sum_{i=1}^{N} \sum_n q_i S(r_m - r_i - nL)$$
$$\approx \sum_{i=1}^{N} q_i S(r_{im}^{min}).$$

Here (and below) we use m as an index for mesh points that lie within the primary box. There are $N_m = (L/h)^3$ mesh points per box in a simple cubic array with a distance h between each point and its nearest neighbors. The label n runs over all boxes and $r_{im}^{min}$ is the vector from mesh point m (at $r_m$ in the primary box) to the nearest image of particle i. The final approximate equality of Equation (22) follows because the charge spreading function is chosen to fall off rapidly to zero with distance, so each mesh point can only receive a contribution from at most one image of any particular particle (strictly speaking, this will be an approximation in cases where S(r) merely decays rapidly and does not identically vanish beyond some distance). The number of mesh points $N_S$ over which S(r) is non-zero (or cannot reasonably be approximated by zero) is the support of S(r) and partially determines the computational expense of the charge spreading step: for each charge i, $S(r_{im}^{min})$ must be evaluated at $N_S$ mesh points. Since charge-spreading (together with the analogous force calculation described below) turns out to include a majority of the computation it would be desirable that S(r) has a small support. Unfortunately, using very small supports tends to lead to larger errors in the overall calculation due to the finite mesh size, so an appropriate balance must be found. Note that the object of charge spreading is not to try and reproduce something as close to the original point charge distribution as possible, nor even to try and reproduce $\rho_\sigma$. Since the final result (i.e. energies and forces) is paramount, the object of charge spreading is merely to transfer the charges to the mesh in a well defined way, so that further manipulations can rapidly lead to an accurate final result.

The general approach to computing the energy E or the force on each particle from $\rho^S(r)$ is to first compute $\phi^*(r) = \rho^S(r) \otimes \gamma(r) \otimes U(r)$ at grid locations (86). From $\phi^*(r)$ grid samples of the potential function can be computed as $\phi_\sigma(r) = \phi^*(r) \otimes T(r) = \rho^S(r) \otimes \gamma(r) \otimes U(r) \otimes T(r)$ (illustrated as 90) assuming that $G_\sigma(r) = S(r) \otimes U(r) \otimes T(r)$. The value of $\phi_\sigma(r)$ can be computed at the nonzero locations of $\rho(r)$ (94) in order to compute $$E = \frac{1}{2}\rho \cdot \phi_\sigma$$

(92). An alternative is to compute a spread charge distribution $\rho^T = T \otimes \rho$ (96) and then to compute $$E = \frac{1}{2}\rho^T \cdot \phi^*$$

(98). This computation of the forces is discussed in more detail below. Note that S(r) and T(r) can be chosen to be equal but are not necessarily so, and U(r) can be omitted entirely. Also, the grid-based computation of $\phi^*(r)=\rho^S(r)\otimes\gamma(r)\otimes U(r)$ can be computed directly in the spatial domain, or alternatively, can be computed in a fast Fourier transform (FFT) domain. Similarly, the energy E can be computed in the FFT domain.

The force computation step is almost identical to charge spreading, although perhaps less intuitively obvious. The force is a result of a convolution of a potential $\phi^*$ and a second (vector) function, which we write as $$T'(r) = \frac{dT}{dr}$$

where the scalar function T is even and is often chosen to be the same as the charge spreading function S. To see why this is so, it is first important to realize that the potential $\phi^*$ is not typically a mesh-based representation of $\phi_\sigma$. Instead, it is arranged (as explained below) that $\phi^*$ is the potential for which some pre-chosen interpolation function T satisfies $\phi_\sigma=T\otimes\phi^*$. This is quite analogous to the observation that the charge distribution arising from the charge spreading step does not have to be a mesh-based approximation of either $\rho_\sigma$ or $\rho$ as long as the final forces and energies are calculated correctly. From Equation (16) and Equation (18) we find $$E = \frac{1}{2}\rho \cdot (\phi^* \otimes T) = \frac{1}{2}(\rho \otimes T) \cdot \phi^* = \frac{1}{2}\rho^T \cdot \phi^* \qquad (23)$$

where $\rho^T=\rho\otimes T$ is defined analogously to $\rho^S$. If the energy is calculated in real space (as is necessarily the case for real space methods) then Equation (23) simply says that one could either use the convolution with T to take the off-mesh charges to the on-mesh electrostatic potential, or alternatively use it to take the charges to the potential. Differentiating Equation (23) gives the force on the $i^{th}$ particle as $$F_i^\sigma = -\frac{\partial \rho^T}{\partial r_i} \cdot \varphi^*,$$

and further manipulation shows this may be rewritten $$F_i^\sigma = q_i F^\sigma(r_i) \text{ where } F^\sigma = T'\otimes\phi^*, \qquad (24)$$

as stated above. In practice, and analogously to Equation (22), the force will be evaluated as a mesh convolution $$F_i^\sigma = q_i h^3 \sum_{m(r_i,T)} \phi^*(r_m)T'(r_{im}^{min}), \qquad (25)$$

where $m(r_i,T)$ runs over the points of support for $T(r_{im}^{min})$.

Figure 7C:
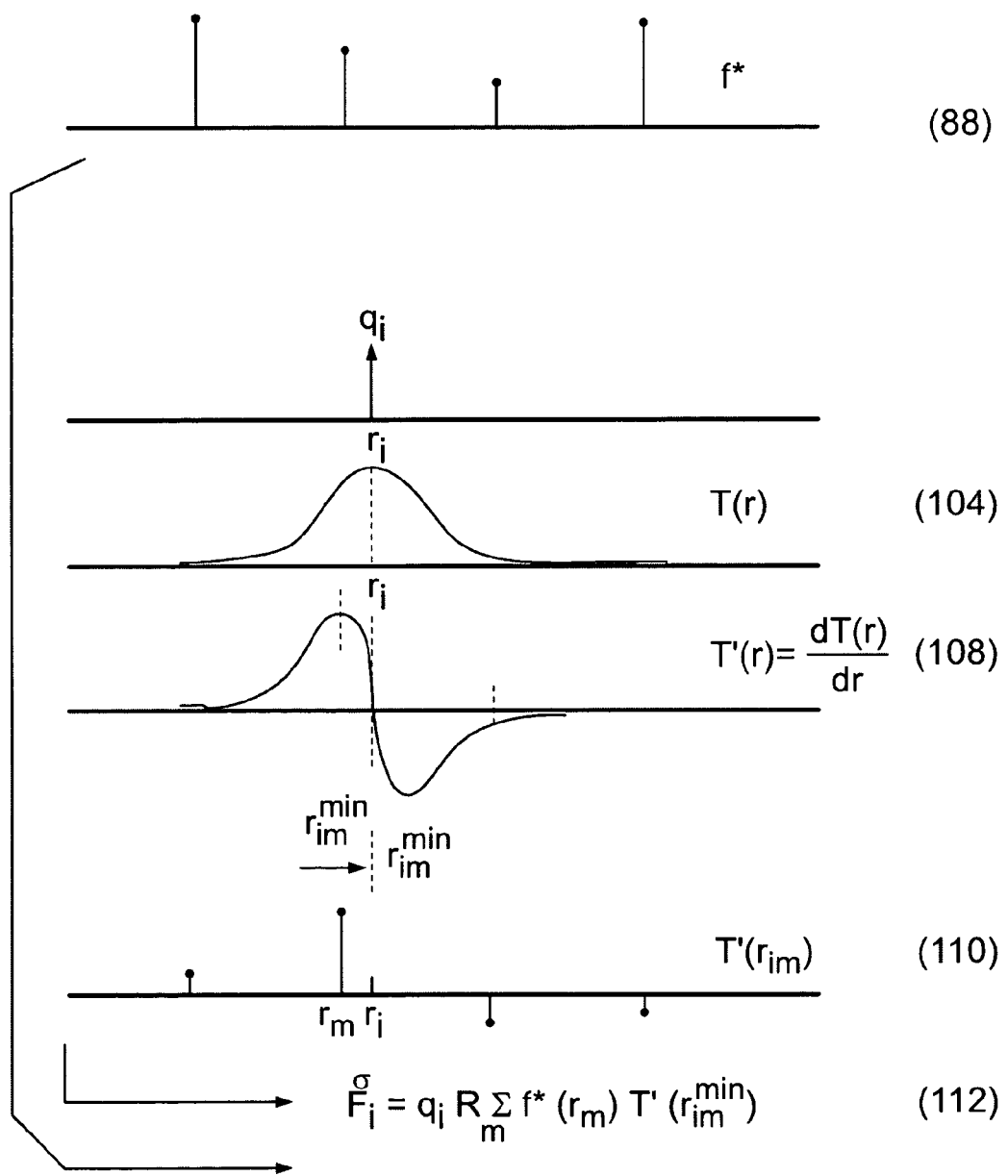
Figure 8:
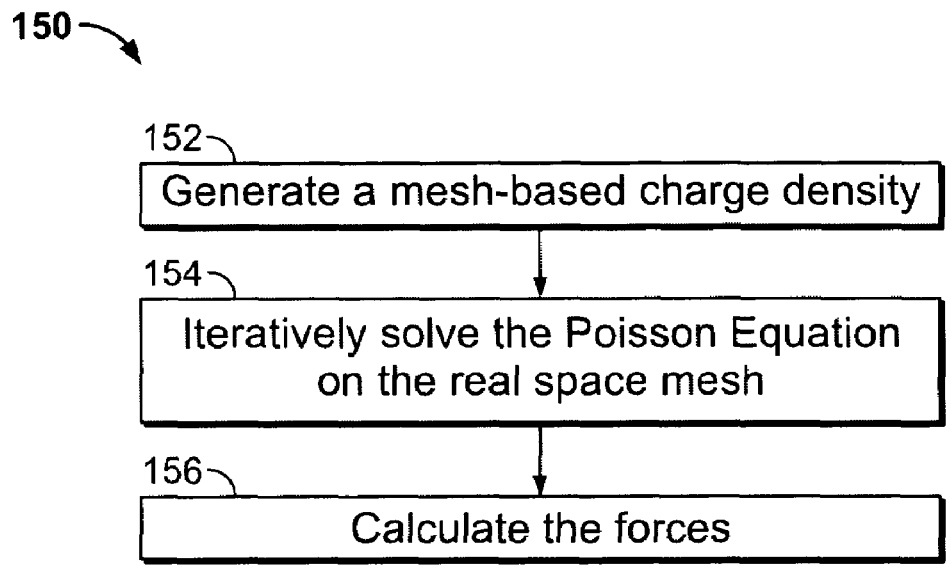
FIG. 8 is a flow chart.

Referring to FIG. 7C computation of the force on the $i^{th}$ particle from the grid values of $\phi^*$ (88) involves applying the spreading function T(r) (104) to the charge distribution to each charged particle, such as the particle at $r_i$ by first computing its vector of spatial derivatives $$T'(r) = \frac{d}{dr}T(r)$$

(108) and then evaluating these spatial derivatives, centered at the particle location $r_i$, at grid locations $r_m$ (110). The force component $F_i^o$ on the $i^{th}$ particle is then computed using the direct sum over grid locations of $\phi^*$ (88) and the samples of the spatial derivatives of the spreading function $T'(r_{im}^{min})$ (108).

Referring to FIG. 2 a real space method 50 is shown. Method 50 includes generating 152 a mesh-based charge density using $\rho^S=\rho\otimes S$. Method 150 also includes iteratively solving 54 the Poisson Equation $\nabla^2\phi^*=-4\pi\rho^S$ on the real space mesh using a discrete representation of $\nabla^2$. For example, multigrid and SOR methods can be used. This yields $\phi^*=\gamma\otimes\rho^S$. Subsequently, method 150 includes calculating 156 the forces from $F_i^o=q_iT'\otimes\phi^*$. If the electrostatic potential at the particle positions is required it may be calculated from $\phi_\sigma=\phi^*\otimes T$, and the energy follows from $$E = \frac{1}{2}\rho \cdot \phi_\sigma.$$

Since it is desired to recover $\phi_\sigma=\rho\otimes G_\sigma\otimes\gamma$, this implies S and T be chosen so that $S\otimes T=G_\sigma$. One choice is $S=T=G_{\sigma/\sqrt{2}}$, which has the advantage (in the case where $\phi_\sigma$ is not required) that it removes the need to perform a convolution for the energy, which is obtained from $$E = \frac{1}{2}\rho^S \cdot \phi^*.$$

Figure 9:
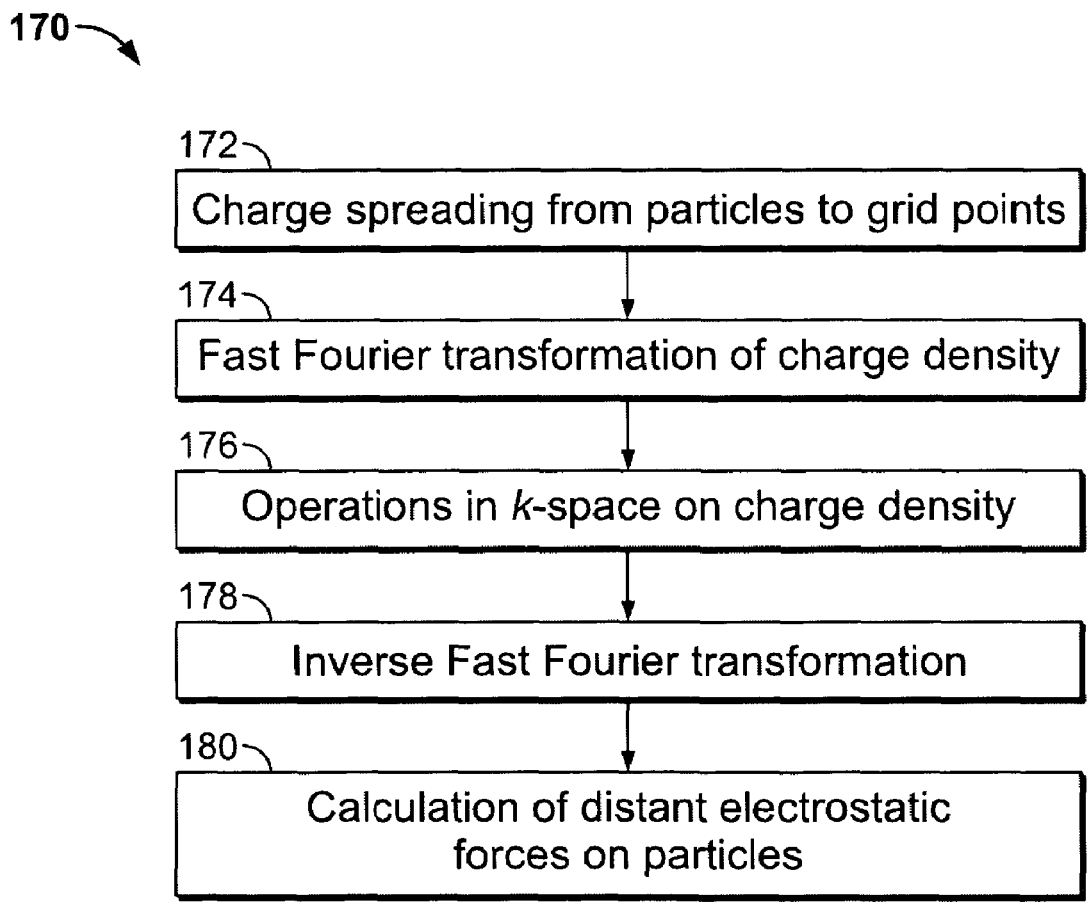
FIG. 9 is a flow chart.

Referring to FIG. 9, a FFT based Ewald method 170 is shown. Method 170 includes generating 172 a mesh-based charge density using $\rho^S=\rho\otimes S$ and performing 174 the FFT $\rho^S\rightarrow\tilde{\rho}^S$. Method 170 includes solving 176, in k-space, a modified Poisson equation $\phi^*=\gamma_{mod}\otimes\rho^S$, which is approximately $\tilde{\phi}_k^*=\tilde{\gamma}_{mod}(k)\tilde{\rho}_k^S$. Method 170 also includes calculating the energy $$E_\sigma = \frac{1}{2}\rho \cdot (T \otimes \phi^*) = \frac{V}{2}\sum_k \frac{\tilde{T}(k)}{\tilde{S}(k)}\tilde{\gamma}_{mod}(k)|\tilde{\rho}_k^S|^2$$

(S=T in some examples). Subsequent to the energy calculation, method 170 included performing 178 an inverse FFT $\tilde{\phi}^*\rightarrow\phi^*$ and calculating 180 the forces from $F_i^o=q_iT'\otimes\phi^*$. If the electrostatic potential at the particle positions is required it may be calculated from $\phi_\sigma=\phi^*\otimes T$.

Writing out the contributions to the electrostatic potential explicitly, results in the equation $$\phi_\sigma=\rho\otimes S\otimes\gamma_{mod}\otimes T, \qquad (26)$$

and since $\phi_\sigma=\rho\otimes G_\sigma\otimes\gamma$, this implies S and T and $\gamma_{mod}$ be chosen so that $$S\otimes\gamma_{mod}\otimes T=G_\sigma\otimes\gamma. \qquad (27)$$

One choice is $S=T=G_{\sigma/\sqrt{2}}$ with $\gamma_{mod}=\gamma$ is possible. However, enforcing $\gamma_{mod}=\gamma$ requires $S\otimes T=G_\sigma$, and thus the full width of $G_\sigma$ must come from the convolutions with S and T just as in the real space method. Instead, by performing an additional convolution in reciprocal space (which is computationally trivial) the amount of spreading in real space can be much diminished, significantly speeding up the calculation by much reducing the support required for S and T. The additional reciprocal space convolution U is a modification of the Poisson Green function, i.e. $\gamma_{mod}=U\otimes\gamma$. A possible choice is S=T and U chosen such that $G_\sigma=S\otimes U\otimes T$. Other choices do not necessarily has S equal T.

An alternative to use of Gaussian distributions is to use as low an order of B-spline function as possible to minimize the support, however higher order B-splines are smoother functions and lead to smaller errors due to the discrete operations, so there are competing effects and typically the optimum B-spline used to represent a charge extends over more than the nearest mesh points, but its support is much less than that of $G_{\sigma/\sqrt{2}}$.

Equation (26) provides a framework in which most of the various mesh Ewald methods may be summarized in a consistent form. These methods differ principally in their choices of S, T and $\gamma_{mod}$ functions and the mathematical space in which the Poisson equation is solved. Equation (27) provides a simple but important criterion by which choices of S, T and $\gamma_{mod}$ can be evaluated.

Gaussian-Split Ewald Method

The Gaussian-split Ewald (GSE) method can be used both with a real space and reciprocal space methods of solving the Poisson equation. GSE involves two stages of charge spreading. First, charges are spread to the mesh by convolving with a function with small support. The small support ensures that the operation is rapid. Then a second convolution (with U) is performed to further spread the charges, which is very fast since it can be performed on-mesh in the real space version r-GSE (in the k-space version, k-GSE this second convolution is done in k-space). The final interpolation step to calculate the forces is also performed rapidly by convolving with a function (T) with small support. In this embodiment, spreading functions are chosen to satisfy Equation (27).

From Equation (27) we know that, with choice of standard Green function (i.e. $\gamma_{mod}=\gamma$) S and T should satisfy $S\otimes T=G_\sigma$. A two stage charge spreading method splits S into two parts, so by definition $S=S_1\otimes S_2$, and Equation (27) implies $S_1\otimes S_2\otimes T=G_\sigma$. We choose $S_1=T=G_{\sigma_1}$ and $S_2=G_{\sigma_2}$ with the Gaussian variances satisfying $$2\sigma_1^2+\sigma_2^2=\sigma^2. \tag{28}$$

Substituting the GSE choice of S, $\gamma_{mod}$ and T into Eq. (26), we find $$\phi_\sigma=\rho\otimes G_{\sigma_1}\otimes G_{\sigma_2}\otimes\gamma\otimes G_{\sigma_1}, \tag{29}$$

which effectively defines the GSE method. An advantage of this approach is that by tuning the ratio of $\sigma_1/\sigma_2$ GSE allows computational load to be shifted away from the bottleneck charge-spreading and interpolation steps to the highly efficient second charge spreading step (which takes advantage of the fact that an on-grid convolution with a Gaussian is nearly trivial computationally) and it does so without violating Equation (27).

Figure 10:
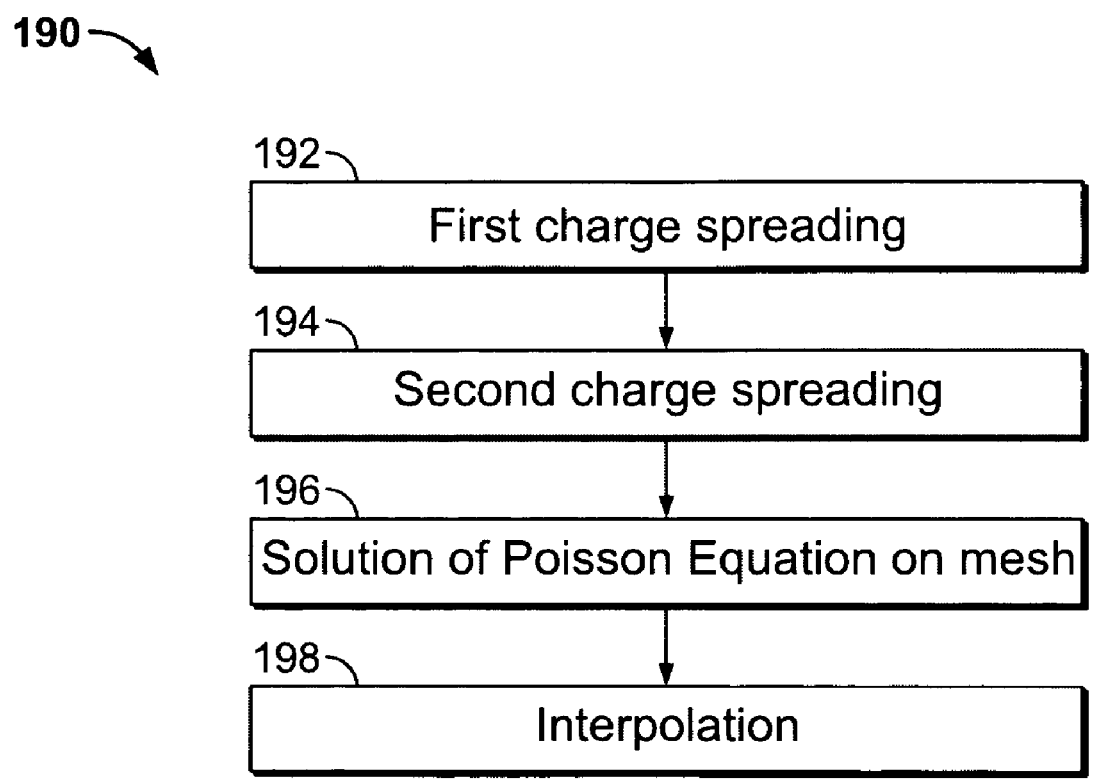
FIG. 10 is a flow chart.

Referring to FIG. 10, corresponding to each convolution in Eq. (18), a process 190 for r-GSE is shown. Process 190 includes a First charge spreading (step 192), for example, $\rho_{\sigma_1}=\rho\otimes G_{\sigma_1}$. In the first charge spreading, each particle charge is spread on the grid by convolving with $G_{\sigma_1}$. From Equation (22), the computation to be performed is $$\rho_{\sigma_1}(r_m) = \frac{1}{(2\pi\sigma_1^2)^{3/2}}\sum_{i=1}^{N} q_i\exp(-|r_{im}^{min}|^2/2\sigma_1^2). \tag{30}$$

Process 190 also includes a second charge spreading (step 194), for example, $$\rho^s = \rho_{\sqrt{\sigma_1^2+\sigma_2^2}} = \rho_{\sigma_1}\otimes G_{\sigma_2}.$$

A second (and more efficient) convolution with $G_{\sigma_2}$ is performed to complete the charge spreading. This convolution is carried out taking advantage of separability of Gaussian functions, which allows the three dimensional Gaussian convolution to be replaced by three trivial one dimensional convolutions (one along each dimension). Using the separability, one convolves each row with a Gaussian (i.e., along the x-axis), then convolves each column of the result with a Gaussian (i.e., along the y-axis), and finally convolves with a Gaussian along the z-axis.

Subsequently, process 190 includes solving the Poisson equation on mesh (step 196), for example using $\phi^*=\rho^S\otimes\gamma$. In r-GSE, using the charge density $\rho^S$ obtained in step (2), the Poisson equation is directly solved in real space using either with SOR or multigrid techniques. For example, a Hermitian discrete representation on the finest grid can be used to achieve higher accuracy. Note that, the mesh based potential could equivalently be written $$\phi^* \equiv \phi_{\sqrt{\sigma_1^2+\sigma_2^2}}.$$

Subsequently, process 190 includes interpolating the potential (step 198), for example using $\phi_\sigma=\rho_{\sigma_1}\otimes\phi^*$ (and $F_i^\sigma=q_iG_{\sigma_1}'\otimes\phi^*$). With the on-mesh potential $\phi^*$ computed, the potential at point $r_i$ may be obtained (if required) by interpolation using $G_{\sigma_1}$ as the interpolation kernel $$\phi_\sigma(r) = \frac{h^3}{(2\pi\sigma_1^2)^{3/2}}\sum_m \exp(-|r_{im}^{min}|^2/2\sigma_1^2)\phi^*(r_m). \tag{31}$$

and the force on particle i is $$F_i^\sigma = \frac{q_i h^3}{(2\pi)^{3/2}\sigma_1^5}\sum_m (r_{im}^{min}\exp(-|r_{im}^{min}|^2/2\sigma_1^2)\phi^*(r_m). \tag{32}$$

Remember that $r_{im}^{min}$ is the vector from mesh point m (at $r_m$ in the primary box) to the nearest image of particle i.

Note that the energy $$E = \frac{1}{2}\rho_{\sigma_1}\cdot\phi^* = \frac{h^3}{2}\sum_m \rho_{\sigma_1}(r_m)\phi^*(r_m)$$

can be calculated on mesh before the interpolation step, provided that the values of $\rho_{\sigma_1}$ on the mesh from step (1) are kept in memory.

While the example above was described in real space, similar splitting of the Gaussian may also be used with an FFT approach. In k-GSE the second charge spreading step is done as a multiplication in reciprocal space (which we write as a modification of the Green function), i.e. $\phi_o = \rho \otimes G_{o1} \otimes (G_{o2} \otimes \gamma) \otimes G_{o1} = \rho \otimes G_{o1} \otimes (\gamma_{mod}) \otimes G_{o1}$. Steps (1) and (4) of k-GSE are algorithmically identical to r-GSE, although to be consistent with previous notation we term the charge density produced after step (1) in k-GSE $\rho^S$ [rather than that produced after step (2)]. Instead of steps (2) and (3), the Poisson equation is solved in reciprocal space, i.e. steps (ii), (iii) and (v) of the general FFT Ewald method [see previous subsection] are substituted for steps (2) and (3).

A feature of the GSE approach, common to both the real and k-space implementations, relates to the unified GSE framework as a series of convolutions across each step in the approach: charge spreading, solving the Poisson equation, and calculating forces. For a desired accuracy, the balance between these steps can be varied in a continuous manner by setting the parameter $\kappa$, which (when $\sigma$ for the screening Gaussian charge distribution is given) determines the standard deviation of the Gaussians used in the charge spreading and force calculations:

$$\sigma_1 = \sigma\sqrt{\kappa}\ 0 \leq \kappa \leq \tfrac{1}{2}$$

For a given value of $\sigma$ the value of $\kappa$ also sets the standard deviation of the second Gaussian, according to:

$$\sigma_2 = \sigma\sqrt{1-2\kappa}$$

There are also a number of specific improvements that the GSE method affords to a real space implementation. These improvements effectively serve to accelerate real space computation for a given accuracy requirement by significantly reducing the size of the support number of mesh-based grid points needed in charge spreading and force calculation. Additional benefits for the r-GSE arise from the treatment of the second convolution in real-space. Rather than employ a diffusion scheme this second spreading is implemented as an exact on-mesh Gaussian convolution. Not only is this approach more accurate than the low order discrete representation of the Laplacian operator in the diffusion equation, the convolution can be efficiently computed by exploiting the dimensional separability of Gaussian functions.

A Recipe of Gaussian-Split Ewald Method (GSE) for the Distant Subsystem

The Gaussian-Split Ewald method can be used to calculate the effect of distant electrostatic forces on particles. The method includes charge spreading from particles to grid points, fast Fourier transformation of charge density, operations in k-space on charge density, inverse Fast Fourier transformation, and the calculation of distant electrostatic forces on particles as described above.

GSE involves three independent parameters: the Gaussian standard deviation $\sigma$ shared by a distant subsystem and a middle subsystem, another Gaussian standard deviation $\sigma_r$ used in charge spreading and force calculation, and the grid spacing $\Delta$. Respectively, $\sigma$ and $\sigma_r$ are positively correlated to the distance cutoff in the middle subsystem, and the cutoff of charge spreading and force calculation in the distant subsystem. For reasonable accuracy, distance cutoffs are empirically chosen, $R_c^{mid} = 3.2\sqrt{2}\sigma$ and $R_c^{dis} = 3\sqrt{2}\sigma_r$ for the middle and the distant system. Greater cutoff-sigma ratio may be chosen to achieve higher accuracy. Another Gaussian function is involved in the k-space operations, whose standard deviation in the real-space is $\sigma_k = \sqrt{\sigma^2 - 2\sigma_r^2}$. For example, a GSE parameter set can include:

Grid spacing $\Delta = 2A$, $R_c^{mid} = 13A$, $\sigma = 2.873A$ $R_c^{dis} = 7.04A$, $\sigma_r = 1.659A$ $\sigma_k = 1.657A$ In addition, when a simulation system is given, its side-lengths Lx, Ly and Lz in angstroms, and the number of grid points at each side $Nx = Lx/\Delta$, $Ny = Ly/\Delta$, and $Nz = Lz/\Delta$ are important in the algorithm. It is assumed that we only deal with rectangular/cubic systems.

During the charge spreading, particles of given charges and coordinates are present in the system box, which is covered by a mesh of cubic cells (with grid spacing $\Delta$). The purpose of charge spreading is to assign a charge density value to each grid point in the mesh. Each grid point receives contributions of charges from all the particles within the distance cutoff $R_c^{dis}$. The same cutoff is also applied in the force calculation step later. The charge density contribution from a particle to a grid point is $$\frac{1}{2\sqrt{2}\,\sigma_r^3 \pi^{3/2}} q \exp(-r^2/2\sigma_r^2),$$

where q indicates the particle's charge and $r \leq R_c^{dis}$ the distance between the particle and the grid point. Periodical boundary conditions should be maintained in charge spreading. Specifically, a grid point should receive charge contributions from particles in the simulation system as well as its mirror systems, as long as they are within the distance cutoff. The accumulation of charges at grid points result in a charge density $\rho(i,j,k)$ that is defined on the mesh, with i,j,k being the x,y,z indices of grid points.

During the FFT of charge density on mesh, a 3D FFT is performed, which converts charge density $\rho$ into its k-space representation $\tilde{\rho} = FFT(\rho)$. It should be noted that $\tilde{\rho}$ are complex numbers defined at grid points in a mesh in k-space. The k-space mesh covers kx from $$(-Nx/2+1)\frac{2\pi}{Lx} \text{ to } (Nx/2)\frac{2\pi}{Lx},$$

ky from $$(-Ny/2+1)\frac{2\pi}{Ly} \text{ to } (Ny/2)\frac{2\pi}{Ly},$$

and kz from $$(-Nz/2+1)\frac{2\pi}{Lz} \text{ to } (Nz/2)\frac{2\pi}{Lz},$$

with spacing $$\frac{2\pi}{Lx}, \frac{2\pi}{Ly} \text{ and } \frac{2\pi}{Lz}$$

respectively, where kx, ky, kz are the x, y, z components of the wavenumber vector k. In other words, $\tilde{\rho}$ is indexed by three integers, namely $$i=(-Nx/2+1) \ldots (Nx/2),$$

$$j=(-Ny2+1) \ldots (Ny2), \text{ and}$$

$$k=(-Nz/2+1) \ldots (Nz/2).$$

Because $\rho$ is always real, by properties of Fourier transformations, $\tilde{\rho}$ holds certain symmetry that may exploited in computations. Henceforth, for convenience the real and imaginary components of $\tilde{\rho}$ will be denoted by $\tilde{\rho}_R$ and $\tilde{\rho}_I$ respectively in this document.

As mentioned previously, for performing operations in k-space, each grid point in the k-space may by defined by three indices (i,j,k) or equivalently by a wavenumber vector k=(kx,ky,kz), with $$kx = i\frac{2\pi}{Lx}, ky = j\frac{2\pi}{Ly} \text{ and } kz = i\frac{2\pi}{Lz}.$$

At each k-space grid point reside $\tilde{\rho}_R$, $\tilde{\rho}_I$ and a pre-calculated influence function (a real function)

$$I(k) = \frac{4\pi}{k^2} \exp(-2k^2 \sigma_k^2),$$

where $k^2=kx^2+ky^2+kz^2$. Straightforwardly update $\tilde{\rho}_R(i,j,k) \leftarrow \tilde{\rho}_R(i,j,k)I(i,j,k)$ and $\tilde{\rho}_I(i,j,k) \leftarrow \tilde{\rho}_I(i,j,k)I(i,j,k)$ is carried out at each grid point. Explicitly the influence function at point (i,j,k) is:

$$I(i, j, k) = \frac{4\pi}{\left(i\frac{2\pi}{Lx}\right)^2 + \left(j\frac{2\pi}{Ly}\right)^2 + \left(k\frac{2\pi}{Lz}\right)^2} \exp\left\{-2\left[\left(i\frac{2\pi}{Lx}\right)^2 + \left(j\frac{2\pi}{Ly}\right)^2 + \left(k\frac{2\pi}{Lz}\right)^2\right]\sigma_k^2\right\}$$

After the influence function being applied to $\tilde{\rho}$, a 3-D inverse FFT is performed and electrostatic potential is obtained:

$$\phi = iFFT[I(k)\tilde{\rho}_R(k), I(k)\tilde{\rho}_I(k)]$$

In the FFT calculation, an electrostatic potential $\phi(i,j,k)$ is determined at each grid point indexed by (i,j,k) in real-space this electrostatic potential is used during the subsequent force calculation. The force calculation is similar to charge spreading in that each particle receives a force contribution from the grid points within the distance cutoff $R_c^{dis}$. Specifically, the x,y,z components of the force contributed from grid point (i,j,k)=(g) to a particle (i) is:

$$f_{i,\alpha} = \frac{\Delta^3}{2\sqrt{2}\,\sigma_r^5 \pi^{3/2}} q \exp(-r_{ig}^2 / 2\sigma_r^2) \phi(i, j, k) d\alpha_{ig},$$

where $\alpha=(x,y,z)$, q represents the particle's charge, $r_{ig}$ the distance between the particle and the grid point, $\phi(i,j,k)$ the potential value at the grid point, and $d\alpha_{ig}$ has three components which correspond to the x, y, and z separation between the grid point and the particle (e.g. dx=the particle's x coordinate–x coordinate of grid points (i,j,k) ). For each particle force contributions are accumulated from all the grid points within the cutoff, resulting in the final distant forces asserted on each particle of the system. Periodical boundary conditions should be considered in the same way as in the charge-spreading step.

Energy calculation in GSE is inexpensive, and amounts to summing over each grid pint of the mesh while accumulating the product of grid charge and potential:

$$E_{dis} = \frac{\Delta^3}{2} \sum_{mesh} \rho(i, j, k) \phi(i, j, k).$$

A system can be of varying size and include a variable number of particles. For example, the average side-lengths of simulation systems range from 32A to 256A, and the system may contain 3,000 to 1,700,000 atoms.

Direct Summing of Pairwise Interactions

In both straightforward enumeration of pairwise interactions between bodies, as well as in computation of the direct sum term in the Ewald methods, efficient arrangement of the computations is desirable. One approach uses multiple computational nodes, each responsible for some of the pairwise calculations. These computational nodes can be associated with physical regions, for example, with a box 11 (FIG. 1) being subdivided into smaller cubes, and each cube is associated with particles in that cube and with one of the computational nodes, which maintain data related to those particles.

Computational nodes can be arranged in hardware architecture with communication paths coupling the nodes. For example, nodes can be implemented on sets of ASICS and arranged on processor boards to form such a communication path. The import and export is optimized according to the available communication paths in the architecture. For example, the import and export regions can be selected to optimize or match the communication paths of the architecture.

Figure 11:
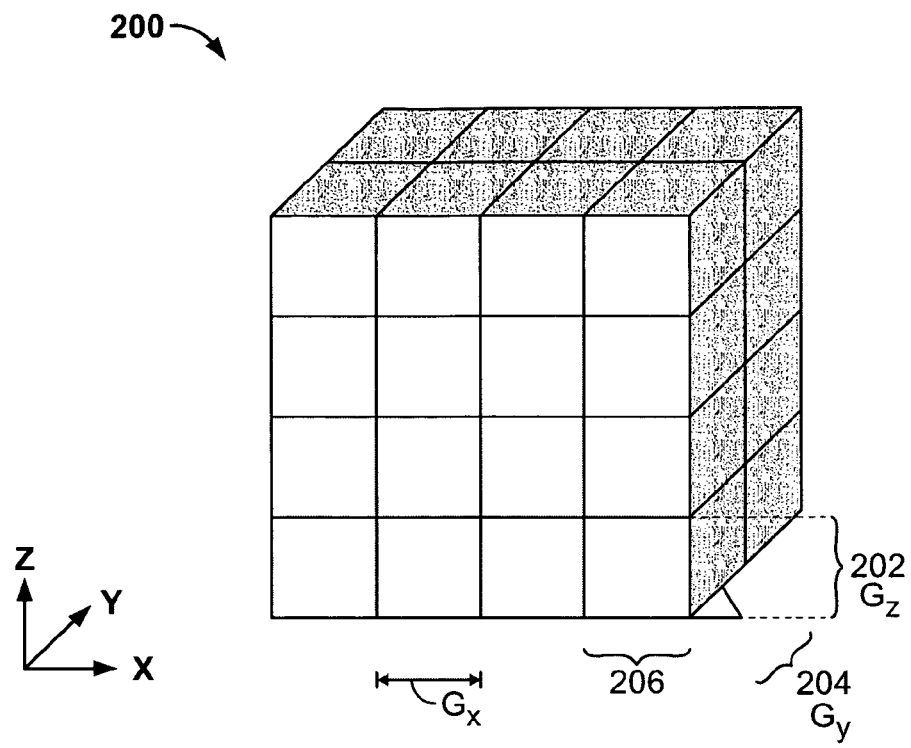
FIG. 11 is block diagram.

Referring to FIG. 11, a system computes interactions for pairs of particles in a computation region 200 through pairwise summation. At the system level, a type of spatial decomposition coordinates the processing of interactions between the particles. The spatial decomposition divides the simulation space 200 into a number of rectangular parallelepipeds (also referred to as boxes) with dimensions $G_x$ (206), $G_y$ (204), and $G_z$ (202) (also shown in FIG. 1). A computation system includes an array of processing elements, each of which takes as input a pair of particles and produces either the force on one particle due to the other or the potential energy contribution from the pair.

Figure 12:
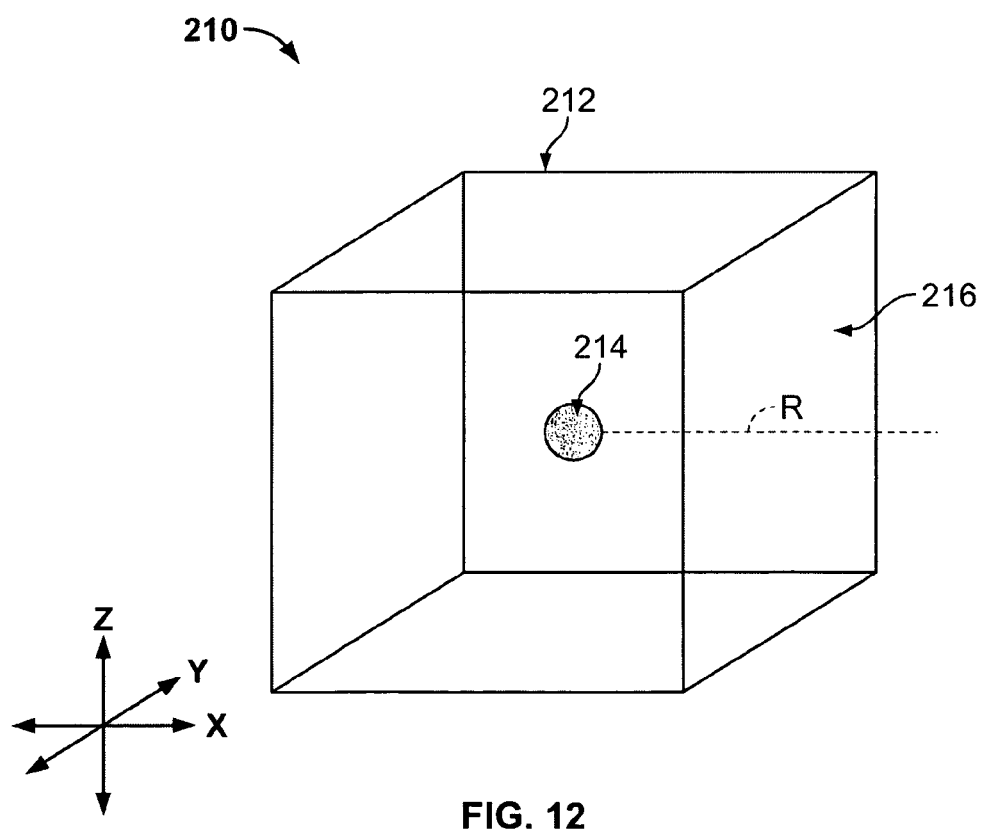
FIG. 12 is block diagram.

Referring to FIG. 12, as described above, the simulation space 200 is divided into multiple packed rectangular parallelepipeds 212. Under this assumption, the interaction neighborhood 210 of a given home box (H) is defined as a region of space surrounding the home box that consists of the locus of all points outside of the home box that lie within a distance R (216) of a point in the home box.

The surface boundary of a single home box can be divided into 26 subregions including six face regions, twelve edge regions, and eight corner regions. The six face regions, denoted $\gamma_{-x}$, $\gamma_{+x}$, $\gamma_{-y}$, $\gamma_{+y}$, $\gamma_{-z}$ and $\gamma_{+z}$, are associated with one of the six faces of the home box. Face region $\gamma_{-x}$, for example, is an hy×hz×R box whose base is the low-x-coordinate face of the home box, and which extends outward from the home box in the −x direction for a distance R. Twelve edge regions, denoted $\gamma_{-x-y}$, $\gamma_{-x+y}$, $\gamma_{+x-y}$, $\gamma_{+x+y}$, $\gamma_{-x-z}$, $\gamma_{-x+z}$, $\gamma_{+x-z}$, $\gamma_{+x+z}$, $\gamma_{-y-z}$, $\gamma_{-y+z}$, $\gamma_{+y-z}$ and $\gamma_{+y+z}$, are associated with one of the twelve edges of the home box. Edge region $\gamma_{-x-y}$, for example, is an "outward-pointing" quarter-cylinder of radius R and length hz whose axis coincides with the low-x-, low-y-coordinate edge of the home boxH. The eight corner regions, are denoted $\gamma_{-x-y-z}$, $\gamma_{-x-y+z}$, $\gamma_{-x+y-z}$, $\gamma_{-x+y+z}$, $\gamma_{+x-y-z}$, $\gamma_{+x-y+z}$, $\gamma_{+x+y-z}$ and $\gamma_{+x+y+z}$, each associated with one of the eight corners of the home box. Corner region $\gamma_{-x-y-z}$, for example, is an "outward-pointing" octant of a sphere of radius R whose center coincides with the low-x-, low-y-, low-z-coordinate corner of the home box.

As described above, the simulation space box 200, referred to as the global cell, is partitioned into a number of smaller boxes, each associated with a single station in a single processing node and referred to as the home box associated with that station. A particle p whose position coordinates fall within a given home box will be described as residing within the home box, and the home box will be referred to as the home box of p.

Figure 13:
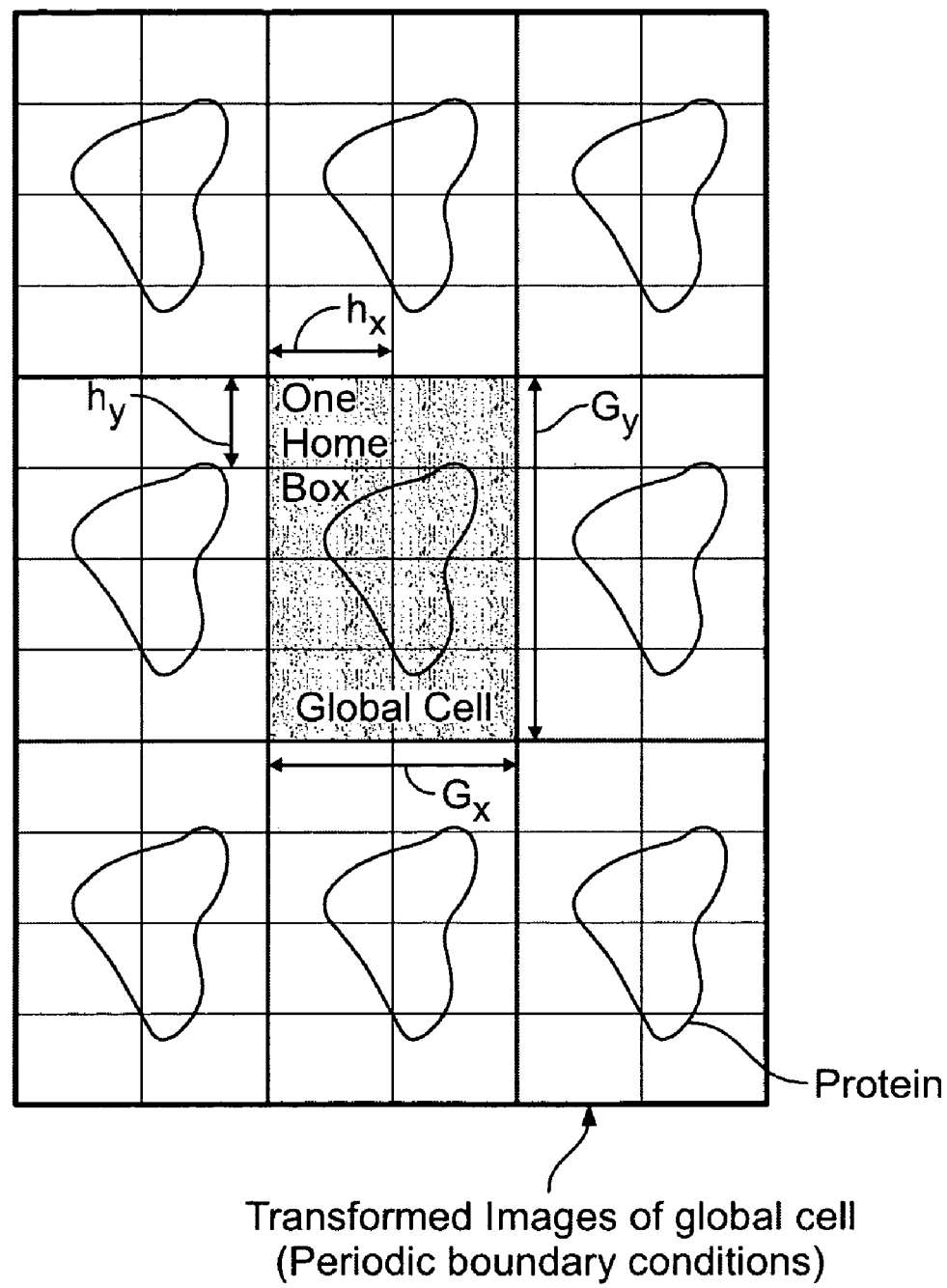
FIG. 13 is block diagram.

Referring to FIG. 13, the dimensions $h_x$, $h_y$ and $h_z$ of each home box are chosen in such a way that $G_d = g_d h_d$ for d∈{x, y, z}, where $g_x$, $g_y$ and $g_z$ are constrained to be integral powers of two whose product is equal to the number of stations in the segment. Subject to these constraints, the $g_d$, and the dimensions of the home box, will be chosen in such a way as to minimize inter-station communication traffic. To avoid irregularities in that portion of the solvent lying along its boundaries due to the existence of the boundary, the global cell serves as the unit cell of an infinite, spatially periodic system with period G=($G_x$, $G_y$, $G_z$). Thus, a molecule near the +x boundary of the global cell, for example, will interact locally with another molecule near the −x boundary having similar y and z coordinates.

The decomposition assigns each processing node a region of space, allowing for nearest-neighbor communications and gives each node responsibility for a subset of particle pairs chosen to limit communication requirements. One example of a spatial decomposition assigns particle pairs to nodes using a "half-shell" method. In the half-shell method roughly, each processing node computes interactions between its own particles and any external particle within the cutoff radius that has a greater x-coordinate. Looking at this in a different manner, given any two particles separated by less than the cutoff, the node that will calculate their interaction is the node that "owns" the particle with the smaller x-coordinate. Recall that for each timestep, every node must import data on the positions and properties of particles with which it must interact, and later export data on the forces or energies due to those interactions. As a result of the half-shell method, each processing node imports data from (and exports data to) a region of the simulation space corresponding to half of a "shell" with thickness equal to the cutoff radius surrounding that node's assigned box.

Figure 14:
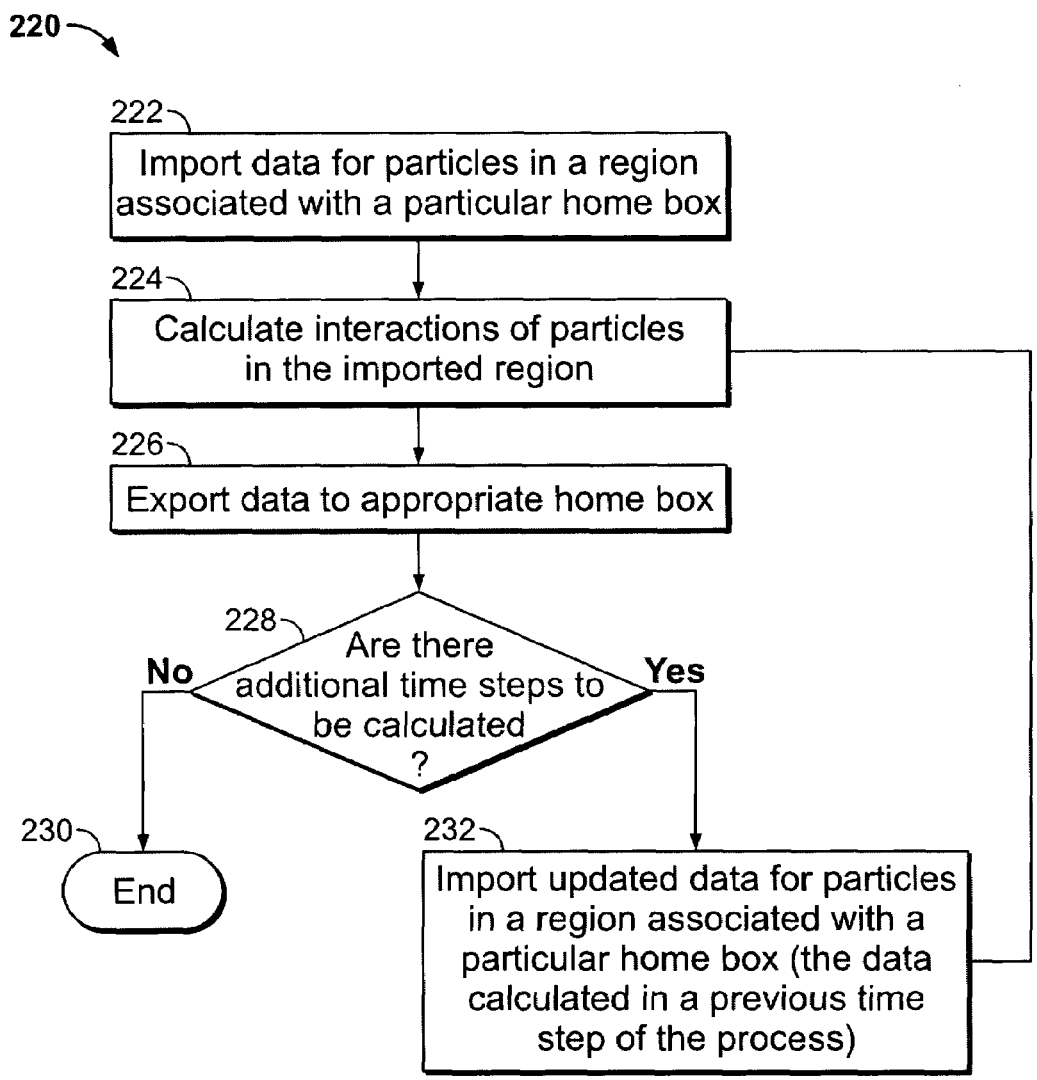
FIG. 14 is a flow chart.

Referring to FIG. 14, at the beginning of each simulation time step, each processing node contain the particle data for those particles currently residing within its home box. During a given time step, however, some (and possibly all) of these particles will need to be interacted with certain particles residing in nearby (in a sense that will depend on the distant interaction scheme) home boxes as well. In order to interact the particles, the processing node imports (step 222) data for particles within a particular region associated with the home box. Using the imported data, the node calculates (step 224) interactions between particles in the combination of the home box and the imported region. The system subsequently exports (step 226) the interaction data to the appropriate home boxes. This process 220 can be performed in parallel on processing nodes for multiple home boxes and regions or alternatively serially on fewer processors. In addition, the process 220 can be iterated to produce a series of time based positions and forces for particles in the system. If multiple time steps are to be calculated, the system determines (step 228) if time steps remain and if so, imports the updated data (step 232) (e.g., data from the previous time step) for particles in the associated calculation region for the home box. The process subsequently calculates (step 224) the interactions and exports (step 226) the data to the appropriate home box.

Figure 15:
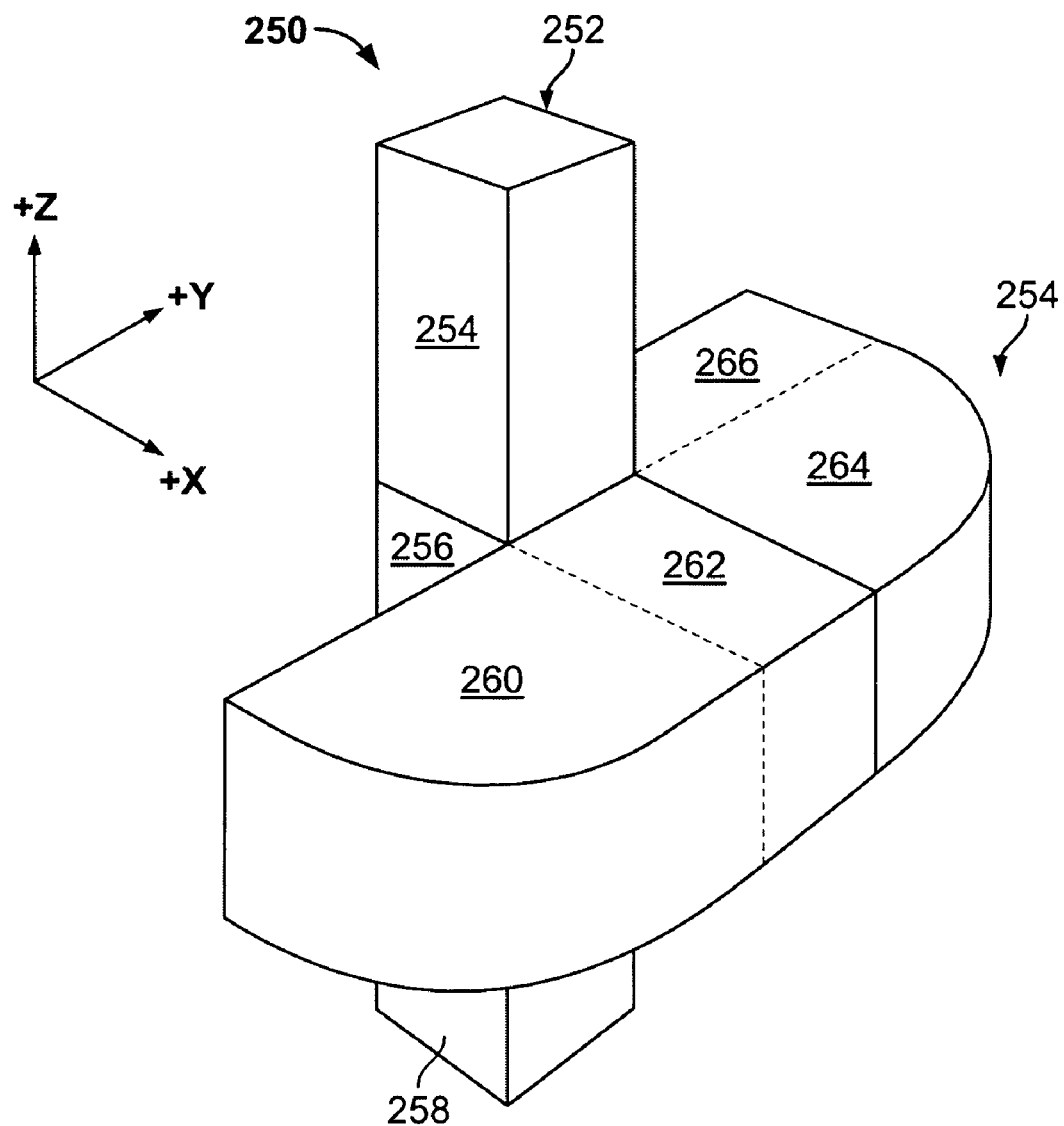
FIG. 15 is block diagram.
Figure 16:
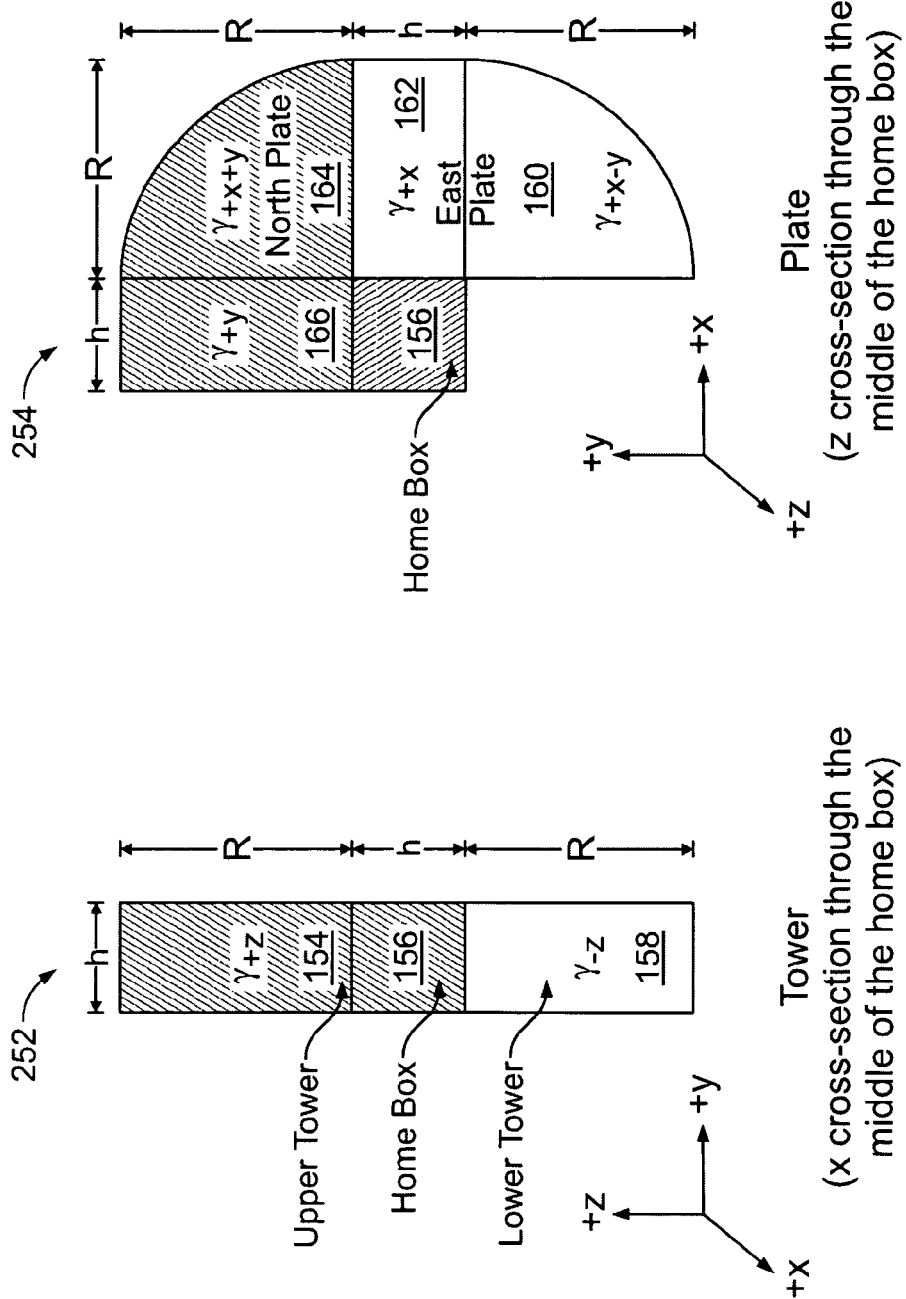
FIG. 16 is block diagram.

As shown in FIGS. 15 and 16, a decomposition of the simulation space based on "orthogonal" data import and interaction regions (referred to as the orthogonal method) is shown. In this decomposition, given any two particles separated by less than the cutoff, the node that calculates the interaction of the pair of particles is the node that owns the box in the x–y plane of the particle with the greater x-coordinate and in the z-line of the particle with the smaller x-coordinate. The result of this distribution of computation is that each node must import data from (and export data to) a certain column 252 (called the tower) and a certain slab 254 (called the plate) of the simulation space. This method has advantages over the half-shell method, including less communication when the cutoff radius is large compared to the box size.

Assuming continuous decomposition, the import region 150 of the orthogonal method consists of the union of four face regions ($\gamma+x$, $\gamma+y$, $\gamma-z$ and $\gamma+z$) and two edge regions ($\gamma+x-y$ and $\gamma+x+y$), but includes no corner regions. The lack of corner regions is a feature that accounts for its advantage over the half-shell method. For convenience, certain portions of the import region are given names. In particular, $\gamma+z$ is referred to as the upper tower 254, while $\gamma-z$ is referred to as the lower tower 258. The union of the upper tower 254 and the lower tower 258 is referred to as the outer tower, while the union of the outer tower and the home box 256 is referred to simply as the tower. The union of subregions $\gamma+y$ 266 and $\gamma+x+y$ 264 is referred to as the north plate, while the union of $\gamma+x$ 262 and $\gamma+x-y$ 260 is referred to as the east plate. The union of the north and east plates is referred to as the outer plate, while the union of the outer plate and the home box is referred to simply as the plate 254. It should be noted that the home box 256 belongs to both the tower 252 and the plate 254. Intuitively, the tower 254 is the box that would be obtained by stretching the home box 256 by a distance R in both the positive z and negative z directions. The plate includes the home box 256 and an adjacent "terrace" of thickness $h_z$ extending (roughly speaking) a distance R away from the tower, but continuing only part of the way around it. The import region employed by the orthogonal method (assuming continuous decomposition) is illustrated in FIGS. 15 and 16.

Figure 17:
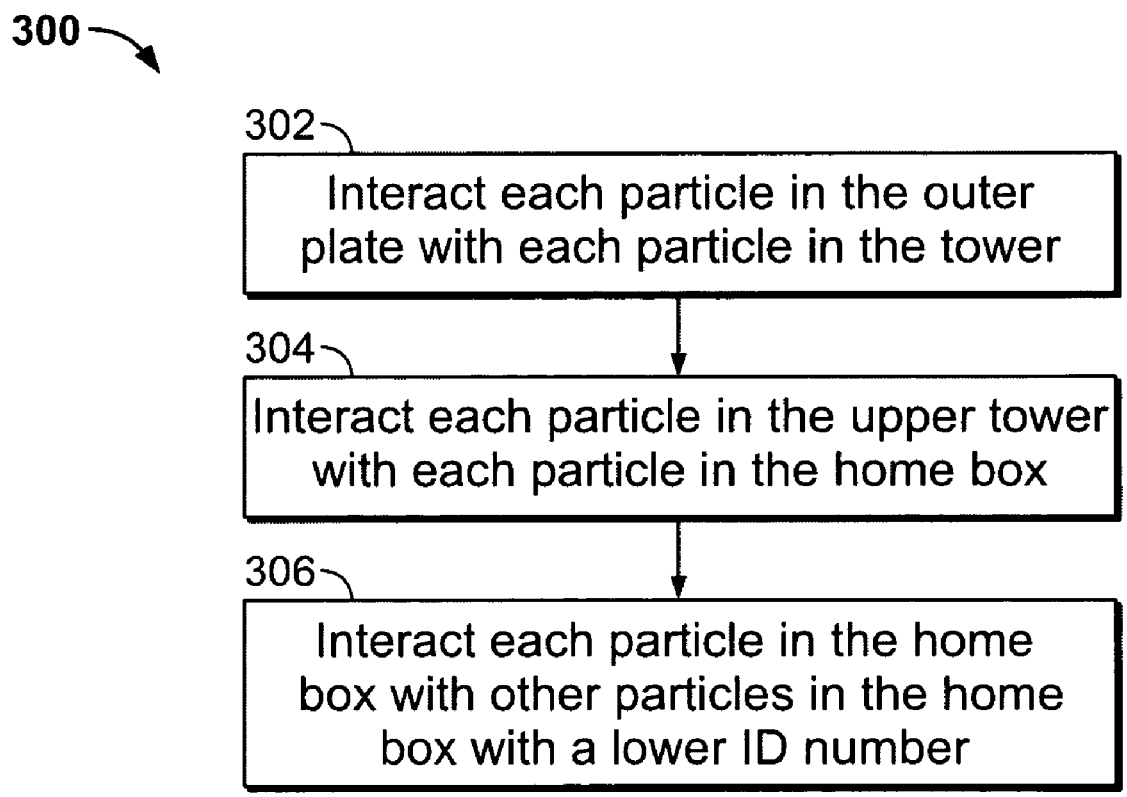
FIG. 17 is a flow chart.

Referring to FIG. 17, using the orthogonal method, the processing node associated with each home box executes a particular subset of the set of interactions required during a given time step. In particular, the set of interactions executed within the station associated with home box is defined such that particles are only interacted if separated by a distance of no more than R and each pair of particles is interacted only one time. Each particle p in the outer plate of the home box is interacted with each particle in its tower 302 (rule 1). Each particle p in the home box is interacted with each particle in the upper tower of the home box 304 (rule 2a). Additionally, each particle p in the home box is interacted with each particle p' in the home box (or overlap region) for which pid (p')>pid (p), where pid (p) is the particle identification number of particle p 306 (rule 2b).

These interaction rules reveals that each interaction occurring within the station associated with the home box involves one particle from the tower of the home box and one particle from the plate of the home box. Although one or both of these particles may reside within the home box itself (which by definition belongs to its own tower and plate), it will often be the case that neither particle resides within the processing node in which they interact, since interaction rule 1 allows a particle in the outer plate of a given home box to be interacted with a particle in the outer tower of that home box. This stands in contrast with the half-shell method, in which each pairwise particle interaction occurring within a given station involves at least one particle that resides within that station's home box. The calculation of potential energy follows the same procedure outlined above for the half-shell method, as does the local accumulation of force vectors. In the orthogonal method, however, when neither of the two interacted particles resides within home box H, a force contribution is exported to the home boxes of both of these particles. Along the way to these home boxes, each such force component is combined with other force components bound for the same destination particle. In the typical case of a home box whose side length is smaller than R, the half-shell method will result in the interaction of a relatively small number of particles residing within its home box with a much larger number of particles that must be imported from other home boxes. In the orthogonal method, the number of interactions occurring within each home box is roughly the same as in the half-shell method, but these interactions are obtained by importing a roughly equal number of particles from its outer tower and outer plate. Just as the perimeter of a square is smaller than that of any other rectangle of equal area, balancing the number of pRecs imported from the tower and plate tends to minimize the amount of data that has to be imported (a rough analog of the perimeter of a rectangle) in order to execute a given number of interactions (a rough analog of its area). A similar argument can be made to explain the advantage of the orthogonal method in exporting and combining pairwise force vectors.

Communication Requirements

This section provides a quantitative estimate of the communication requirements for the orthogonal method, assuming continuous decomposition and (for simplicity) a cubical home box with $h_x=h_y=h_z=h$. Note that in this case, the volumes of a single face region, edge region, and corner region of the home box are given by $V_f = h^2 R$ $V_e = \pi h R^2/4$ $V_c = \pi R^3/6$, The volume of the half-shell method's import region is $V_h = 3 V_f + 6 V_e + 4 V_c$, which is $O(h^2 R + h R^2 + R^3)$, The import region for the orthogonal method is the summation of the 4 face regions and the two edge regions:

$V_o = 4 V_f + 2 V_e$, which is $O(h^2 R + h R^2)$. Taking constant factors into account, we find that the orthogonal method is associated with a smaller import volume (and a smaller number of pRecs that need to be imported) whenever $4(V_e + V_c) > V_f$, or equivalently, whenever $$h \leq \frac{(3\pi + \sqrt{24 + 9\pi^2})R}{6} \approx 3.34R.$$

The analysis above assumes a cubic home box and may underestimate the advantages of the orthogonal method relative to the half-shell method, since the selection of a non-cubic home box may provide additional savings in the amount of data that must be imported by the former. Specifically, if we keep $h_x=h_y$, but allow $h_z$ to vary, the optimum ratio of $h_z$ to $h_x$ and $h_y$ decreases as the number of PNs becomes larger and the volume of each home box consequently becomes smaller. The optimal aspect ratio for the home box chosen for use with the orthogonal method, however, depends on the size and organization of the machine segment.

Although the above analysis has been cast in terms of the import of particle data records into the home region, the same analysis holds for the export of force vectors to those home boxes from which the imported particles were obtained. The analysis is also easily adapted to the case in which distant interactions are handled using one of the box decomposition schemes. In this case, the γ subregions are all boxes and the boundaries of the import regions associated with the two import methods are planar, but the asymptotic results are identical.

Note that the above analysis takes into consideration only the amount of data that must be imported and exported during each simulation time step, and does not take account of the overlap between communication and computation. In most cases, however, it is expected that all tower particle data records (but not all plate particles) will have to be imported before the calculation of pairwise forces can begin. This may represent a disadvantage of the orthogonal method relative to the half-shell method, in which computation can, in principle, begin as soon as the first pRecs are imported into the home box. This disadvantage would be mitigated, however, by a larger ratio of $h_z$ to $h_x$ and $h_y$; in particular, a cubical home box (which may prove advantageous for other reasons) would, for most realistic parameter sets, result in less time being required for tower import than plate import, at the cost of a relatively modest increase in total import volume. It may also be possible to use multithreading techniques to effectively overlay a second simulation on top of the first, overlapping communication in the first simulation with computation in the second and thus "hiding" some or all of the time required for importing tower atoms.

To verify that the orthogonal method causes each pair of particles separated by no more than a distance R to be interacted exactly once, it is useful to distinguish four cases according to whether the home boxes of the two particles have the same coordinates in one or more dimensions. These cases can include if the two home boxes have different x coordinates (case 1), else if the two home boxes have different y coordinates (case 2), else if the two home boxes have different z coordinates (case 3), and else (case 4). Case 2, for example, corresponds to a situation in which the home boxes of the two particles have the same x coordinate, but different y coordinates, with the z coordinate being either the same or different.

In case 1 case, the home boxes of the two particles have different x coordinates. Let t be the point with the smaller x coordinate and p be the other particle, with Ht and Hp defined as their respective home boxes. Now consider the point $s=(s_x, s_y, s_z)=(t_x, ty, pz)$, which is the intersection of (a) the line parallel to the z axis that contains particle t, and (b) the plane normal to the z axis that contains particle p. Since we've assumed that particles p and t are separated by no more than R, it must certainly be the case that $|tz-sz|=|tz-pz|\leq R$. Since tx=sx, ty=sy, and $|tz-sz|\leq R$, particle t must reside within the tower of the home box Hs containing point s. Turning now to particle p, we note that $$\sqrt{(s_x-p_x)^2+(s_y-p_y)^2}=\sqrt{(t_x-p_x)^2+(t_y-p_y)^2}\leq \sqrt{(t_x-p_x)^2+(t_y-p_y)^2+(t_z-p_z)^2}\leq R$$

In combination with the assumption that $p_x \geq t_x$ and the fact $H_p$ has the same z-coordinate as $H_s$ by construction, is easily shown to imply that p must lie within the outer plate of Hs. Thus, interaction rule 1 will cause particles t and p to be interacted within home box $H_s$. To verify that these same two particles will not be interacted with each other more than once, note first that because $p_x \geq t_x$, rule 1 will not be triggered (in any home box) when the two particles are interchanged. Moreover, because $H_t$ and $H_p$ have different x coordinates, neither particle can be in the upper tower of the other, so rule 2(a) will not be triggered. Similarly, the fact that $H_t$ and $H_p$ have different x coordinates precludes the possibility that the two particles are in the same home box, so rule 2(b) will never be applicable. Thus, if the spatial relationship between the two particles is described by case 1, it must be the case that they will interact exactly once.

In the second case, the home boxes of the two particles share a common x coordinate, but have different y coordinates. In such second case, let t be the point with the smaller y coordinate and p be the other point, with Ht and Hp again defined as their respective home boxes. Because t and p lie within a distance R of each other, particle p must reside within subregion γ+y of home box $H_t$, which is part of the outer plate of Ht. Thus, the two particles interact within home box Ht pursuant to rule 1. Because subregion γ−y, unlike subregion γ+y, is not included within the outer plate of a given home box, however, the two particles do not interact within home box Hp. Since Ht and Hp have different y coordinates, neither particle can be in the tower of the other and the two particles cannot share a common home box, thus ruling out a redundant interaction based on either rule 2(a) or 2(b).

In the third case, the home boxes of the two particles have the same x and y coordinates, but different z coordinates. Let p be the particle with the smaller z coordinates and t be the other particle, with $H_p$ and $H_t$ defined as their respective home boxes. Because the distance between p and t does not exceed R, particle t must lie within the upper tower of $H_p$, and the two particles interact within $H_p$ as a result of rule 2 (a). Since p falls within the lower tower of $H_t$, however, this rule does not result in the two particles being redundantly interacted within $H_t$. Because $H_p$ and $H_t$ have identical x and y coordinates, there can be no home box that contains p within its outer plate and t within its tower, so rule 1 is never applicable, and cannot result in a redundant interaction. Rule 2(b) is also never triggered, since $H_p$ and Ht have different z coordinates, and can thus never reside within the same home box. Thus, particles p and t interact exactly once in case 3.

In the fourth case, the two particles lie within the same home box, and are interacted within the home box according to rule 2(b). The particle ID number constraint prevents this rule from causing a redundant interaction within the home box. Because the two particles reside within the same home box, rules 1 and 2(a) are inapplicable, and are thus incapable of causing a redundant interaction. Thus, in this case as well, the two particles are interacted exactly once, completing the proof number of embodiments of the invention have been described. Nevertheless, it will be understood that various modifications may be made without departing from the spirit and scope of the invention.

Alternative versions of the system can be implemented in software, in firmware, in digital electronic circuitry, in computer hardware, in other modes of implementation, or in combinations of such modes. The system can include a computer program product tangibly embodied in a machine-readable storage device for execution by a programmable processor. Method steps can be performed by a programmable processor executing a program of instructions to perform functions by operating on input data and generating output. The system can be implemented in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired. Such language can be either a compiled or interpreted language. Suitable processors include, by way of example, either (or both) general and special purpose microprocessors. Generally, a processor will receive instructions and data from read-only memory and/or random access memory. Generally, a computer will include one or more mass storage devices for storing data files. Such devices include magnetic disks such as internal hard disks and removable disks, magneto-optical disks, or optical disks. Storage devices suitable for tangibly embodying computer program instructions and data include all forms of non-volatile memory, including by way of example semiconductor memory devices such as EPROM, EEPROM, and flash memory devices; magnetic disks such as internal hard disks and removable disks; magneto-optical disks; and CD-ROM disks. Any of the foregoing can be incorporated in or supplemented by ASICs (application-specific integrated circuits).

What is claimed is:

1. A method for computing forces on charged particles using a computer system comprising a plurality of physical computing nodes, the method comprising:

processing on the plurality of nodes data for a set of charged particles, each node storing data for a corresponding sub-set of the set of particles within a region associated with the node, the processing including processing in the computer system data characterizing a charge distribution associated with a set of charged particles according to a spreading function and a predefined operation, the spreading function being representable as a convolution of a first spreading function and a second spreading function, the first spreading function representing a different distribution than the second spreading function, the processing of the charge distribution comprising:

applying the first spreading function in a real domain to determine charge values at locations on a grid from the charge distribution;

applying the operation on the grid to the determined charge values on the grid in the real domain;
applying the second spreading function to the result of applying the operation to generate data characterizing forces on the set of charged particles; and
at each node, according to the generated data, updating the data for the corresponding sub-set of the set of particles within a region associated with the node.

2. The method of claim 1 wherein the charge distribution includes a set of point charges.

3. The method of claim 2 wherein each point charge of the set of point charges has an associated charge value ($q_i$) and an associated location ($r_i$).

4. The method of claim 3 wherein at least some of the associated locations ($r_i$) are locations not on the grid.

5. The method of claim 2 wherein applying the first spreading function in the real domain to determine charge values at locations on the grid from the charge distribution includes convolving the set of point charges with the first spreading function.

6. The method of claim 5 wherein convolving the set of point charges with a first spreading function includes computing a distribution according to $\rho(r) \otimes S(r)$, where $\rho(r)$ comprises the charge distribution and $S(r)$ comprises the first spreading function.

7. The method of claim 5 wherein convolving the set of point charges with the first spreading function includes, for each point charge, spreading a charge associated with the point charge to a set of nearby nodes.

8. The method of claim 1 wherein applying the operation on the grid in the real domain includes computing a potential function.

9. The method of claim 8 wherein computing the potential function includes computing a potential value at least some of the grid locations.

10. The method of claim 1 wherein the operation includes a convolution.

11. The method of claim 10 wherein the convolution includes a convolution with a 1/r function.

12. The method of claim 1 wherein the operation comprises a solution of a Poisson function.

13. The method of claim 1 wherein applying the first spreading function includes a convolution with a portion of the spreading function on the grid.

14. The method of claim 1 wherein applying the operation includes computing a potential according to $\phi^*(r) = \rho^s(r) \otimes \gamma(r)$ where $\rho^s(r)$ comprises the charge distribution and $\gamma(r)$ is an operator.

15. The method of claim 14 wherein $\gamma(r)$ comprises a 1/r function.

16. The method of claim 14 wherein at least some of the force terms are associated with non-grid locations.

17. The method of claim 16 wherein the charge distribution includes a set of point charges at non-grid locations ($r_i$).

18. The method of claim 17 wherein at least some of the force terms associated with non-grid locations are associated with the non-grid locations ($r_i$) associated with the point charges.

19. The method of claim 1 wherein applying the second spreading function to the result of applying the operation generates at least some force terms.

20. The method of claim 1 wherein applying the second spreading function to the result of applying the operation includes applying a spatial derivative to the result of applying the function.

21. The method of claim 1 wherein applying the second spreading function to the result of applying the operation includes evaluating a spatial derivative at grid locations.

22. The method of claim 21 wherein evaluating the spatial derivative includes applying the spatial derivative to the result of applying the operation on the grid.

23. The method of claim 1 wherein applying the second spreading function to the result of applying the operation includes computing a potential energy.

24. The method of claim 1 wherein the real domain comprises a real spatial domain.

25. The method of claim 1 wherein the first spreading function is representable as a convolution of a first portion and a second portion, and wherein applying the first spreading function includes applying the first portion to determine charge values at grid locations and applying the second portion on the grid to the values at the grid locations determined by applying the first portion prior to applying the operation.

26. The method of claim 25 further comprising implementing the second portion as a separable function.

27. The method of claim 25 wherein splitting the first spreading function into the first portion and the second portion includes splitting the first spreading function into the first portion and the second portion based on computational complexity.

28. The method of claim 25 wherein splitting the first spreading function into the first portion and the second portion includes splitting the first spreading function into the first portion and the second portion, the first portion being equal to the second portion.

29. The method of claim 25 wherein splitting the first spreading function into the first portion and the second portion includes splitting the first spreading function into the first portion and the second portion, the first portion being unequal to the second portion.

30. The method of claim 29 wherein the first portion is smaller than the second portion.

31. The method of claim 29 wherein the first portion is selected according to an accuracy level for a force calculation.

32. The method of claim 1 wherein applying the second spreading function to the result of applying the operation includes computing values at locations off the grid based on values at the grid locations.

33. The method of claim 1 wherein the first spreading function and the second spreading function comprise Gaussian functions each having a different variance.

34. The method of claim 1 in which the first spreading function comprises a Gaussian function.

35. The method of claim 1 in which the second spreading function comprises a Gaussian function.

36. A method comprising:
using a computer system comprising a plurality of computing nodes, in which each node stores charge distribution data for a corresponding sub-set of a set of particles within a region associated with the node, processing data characterizing the charge distribution according to a spreading function and a predefined operation, the spreading function being representable as a convolution of a first spreading function and a second spreading function, the first spreading function being representable as a convolution of a first portion and a second portion, the second portion being a separable function, the processing comprising:
applying the first portion of the first spreading function in a real domain to determine charge values at locations on a grid from the charge distribution;

applying a second portion of the first spreading function in the real domain;

applying an operation in the real domain on the grid;

applying the second spreading function to the result of applying the operation; and at each node, updating the charge distribution data according to the result of applying the second spreading function.

37. The method of claim 36 wherein the charge distribution includes a set of point charges.

38. The method of claim 37 wherein the each point charge in the set of point charges has an associated charge value ($q_i$) and an associated location ($r_i$).

39. The method of claim 38 wherein at least some of the associated locations ($r_i$) are locations not on the grid.

40. The method of claim 38 wherein applying the first portion of the first spreading function in the real domain to determine charge values at locations on the grid from the charge distribution includes convolving the set of point charges with the first portion of the first spreading function.

41. The method of claim 40 wherein convolving the set of point charges with the first portion of the first spreading function includes computing a distribution according to $\rho(r) \otimes S(r)$ where $\rho(r)$ comprises the charge distribution and $S(r)$ comprises the first portion of the first spreading function.

42. The method of claim 41 wherein convolving the set of point charges with the first portion of the first spreading function includes, for each point charge, spreading a charge associated with the point charge to a set of nearby nodes or the gird.

43. The method of claim 36 wherein applying the second portion of the first spreading function in the real domain includes applying the second portion of the first spreading function as a separable function.

44. The method of claim 36 wherein applying the second potion of the first spreading function in the real domain includes implementing a discrete space convolution.

45. The method of claim 36 wherein applying the second portion of the first spreading function spreads charges over the grid locations.

46. The method of claim 36 wherein applying the operation on the grid in the real domain includes computing a potential function.

47. The method of claim 46 wherein computing a potential function includes computing a potential function at the grid locations.

48. The method of claim 46 wherein the convolution includes a convolution with a 1/r function.

49. The method of claim 36 wherein the operation includes a convolution.

50. The method of claim 36 wherein the operation comprises a solution of a Poisson function.

51. The method of claim 36 wherein the operation includes a convolution with the second portion of the first spreading function.

52. The method of claim 36 wherein applying the operation includes computing a potential according to $\phi^*(r) = \rho^s(r) \otimes \gamma(r)$, where $\rho^s(r)$ comprises the charge distribution and $\gamma(r)$ is an operator.

53. The method of claim 52 wherein $\gamma(r)$ comprises a 1/r function.

54. The method of claim 36 wherein applying the second spreading function to the result of applying the operation generates at least some force terms.

55. The method of claim 54 wherein at least some of the force terms are associated with non-grid locations.

56. The method of claim 55 wherein the charge distribution includes a set of point charges at non-grid locations ($r_i$).

57. The method of claim 56 wherein the force terms at non-grid locations are at the non-grid locations ($r^j$) associated with the point charges.

58. The method of claim 36 wherein applying the second spreading function to the result of applying the operation includes a spatial derivative at grid locations.

59. The method of claim 58 wherein evaluating the spatial derivative includes applying the spatial derivative to the result of applying the operation on the grid.

60. The method of claim 36 wherein the real domain comprises a real spatial domain.

61. The method of claim 36 wherein applying the second spreading function to the result of applying the operation includes computing values at locations off the grid based on values at the grid locations.

62. The method of claim 36 wherein the first spreading function represents a different distribution than the second spreading function.

63. The method of claim 62 wherein the first spreading function and the second spreading function comprise Gaussian functions each having a different variance.

64. The method of claim 36 wherein the first spreading function comprises a Gaussian function.

65. The method of claim 36 wherein the second spreading function comprises a Gaussian function.

66. The method of claim 36 wherein the first portion is unequal to the second portion.

67. The method of claim 36 wherein the first portion is smaller than the second portion.

68. The method of claim 36 wherein the first portion comprises at least an amount of the first spreading function determined to maintain a specified accuracy level.

69. The method of claim 36 wherein applying an operation in the real domain on the grid includes solving Poisson's equation.

70. The method of claim 69 wherein solving Poisson's equation includes iteratively solving Poisson's equation.

71. A method comprising:

using a computer system comprising a plurality of computing nodes, in which each node stores data for a corresponding sub-set of a set of particles within a region associated with the node, processing a charge distribution according to a Gaussian spreading function, the Gaussian spreading function being a convolution of components, the processing including:

spreading the charges to a grid in a first domain based on a first component of the Gaussian spreading function;

applying a function to the charges on the grid in a second domain using a second component of the Gaussian spreading function;

performing a calculation based on a third component of the Gaussian spreading function and the result of applying the function; and at each node, updating the data according to the result of performing the calculation based on the third component.

72. The method of claim 71 wherein the charge distribution includes a set of point charges.

73. The method of claim 72 wherein each point charge included in the set of point charges has an associated charge value ($q_i$) and an associated location ($r_i$).

74. The method of claim 73 wherein at least some of the associated locations ($r_i$) are locations not on the grid.

75. The method of claim 72 wherein spreading the charges to the grid includes convolving the set of point charges with the first component of the spreading function.

76. The method of claim 75 wherein convolving the set of point charges with the first component of the spreading function includes computing a distribution according to $\rho(r) \otimes S(r)$ where $\rho(r)$ comprises the charge distribution and $S(r)$ comprises the first component of the spreading function.

77. The method of claim 75 wherein convolving the set of point charges with the first component of the spreading function includes, for each point charge, spreading the charge to a set of nearby nodes.

78. The method of claim 71 wherein applying the function to the charges on the grid in a second domain using a second component of the Gaussian spreading function includes applying the second component of the spreading function as a separable function.

79. The method of claim 71 wherein applying the second component of the spreading function in the second domain includes implementing a discrete space convolution.

80. The method of claim 71 wherein applying the function to the charges on the grid in the second domain using the second component of the Gaussian spreading function spreads charges over the grid locations.

81. The method of claim 71 wherein applying the function to the charges on the grid in the second domain includes computing a potential function.

82. The method of claim 81 wherein computing the potential function includes computing the potential function at the grid locations.

83. The method of claim 71 wherein the operation includes a convolution.

84. The method of claim 83 wherein the convolution includes a convolution with a 1/r function.

85. The method of claim 71 wherein the operation comprises a solution of a Poisson function.

86. The method of claim 71 wherein the operation includes a convolution with a second portion of the first spreading function.

87. The method of claim 71 wherein applying the operation includes computing a potential according to $\phi^*(r) = \rho^s(r) \otimes \gamma(r)$ where $\rho^s(r)$ comprises the charge distribution and $\gamma(r)$ is an operator.

88. The method of claim 87 where in $\gamma(r)$ comprises a 1/r function.

89. The method of claim 71 wherein performing the calculation based on a third component of the Gaussian spreading function and the result of applying the function generates at least some force terms.

90. The method of claim 89 wherein at least some of the force terms are associated with non-grid locations.

91. The method of claim 90 wherein the charge distribution includes a set of point charges at non-grid locations ($r_i$).

92. The method of claim 91 wherein the force terms at non-grid locations are at the non-grid locations ($r_i$) associated with the point charges.

93. The method of claim 92 wherein applying the second spreading function to the result of applying the operation includes evaluating a spatial derivative at grid locations.

94. The method of claim 93 wherein evaluating the spatial derivative includes applying the spatial derivative to the result of applying the operation on the grid.

95. The method of 71 wherein performing the calculation based on a third component of the Gaussian and the result of applying the function includes implementing a convolution of the result with the third component.

96. The method of claim 71 wherein the first component of the Gaussian spreading function, the second portion of the Gaussian spreading function, and the third portion of the Gaussian spreading function each represent different Gaussian distributions.

97. The method of claim 71 wherein the first domain is a real domain.

98. The method of claim 71 wherein the second domain is an FFT domain.

99. The method of claim 71 wherein applying the function to the charges on the grid in the second domain using the second component of the Gaussian spreading function includes convolving the function with the second portion of the Gaussian spreading function.

100. The method of claim 99 wherein convolving the function with the second portion of the Gaussian spreading function includes multiplying the function with the second portion of the Gaussian spreading function in the FFT domain.

101. The method of claim 71 wherein performing the calculation includes calculating a force.

102. The method of claim 71 wherein the charge distribution comprises a charge distribution representing a protein.

103. A machine-based method comprising:
selecting a first distribution, a second distribution, and a third distribution such that a convolution of the first distribution, the second distribution, and the third distribution is equal to a predefined spreading function;
using a computer system comprising a plurality of computing nodes, in which each node stores data for a corresponding sub-set of a set of particles within a region associated with the node, determining forces on a particle associated with charges based on applying the first distribution and the second distribution in a first computational domain and applying the third distribution in a second computational domain; and
storing data characterizing the determined forces on the particle at a corresponding node.

104. The method of claim 103 wherein determining forces on the particle associated with the charges includes computing charge values at grid locations.

105. The method of claim 104 wherein determining forces on the particle associated with the charges further comprises computing potentials at non-grid locations.

106. The method of claim 104 wherein determining forces on the particle associated with the charges further comprises computing force terms at grid locations.

107. The method of claim 103 wherein applying the third distribution includes applying the third distribution in combination with an operation to the spread charge.

108. The method of claim 103 wherein the first distribution, the second distribution, and the third distribution are Gaussian functions.

109. The method of claim 103 wherein selecting includes selecting the first distribution, the second distribution, and the third distribution based on an acceptable amount of error.

110. The method of claim 103 wherein determining the forces includes a convolution with a 1/r function.

111. The method of claim 103 wherein determining the forces comprises a solution of a Poisson function.

112. The method of claim 103 wherein applying the first distribution and the second distribution in a first computational domain includes convolving at least one of the first distribution and the second distribution with the charge distribution.

113. The method of claim 103 wherein applying the third distribution in a second computational domain includes convolving the third distribution with a set of charges located at grid locations.

114. The method of claim 103 wherein the first domain is a real domain.

115. The method of claim 103 wherein the second domain is a FFT domain.

* * * * *